US011633162B2

(12) United States Patent
Kato

(10) Patent No.: US 11,633,162 B2
(45) Date of Patent: Apr. 25, 2023

(54) RADIATION DETECTOR AND RADIOGRAPHIC IMAGING APPARATUS

(71) Applicant: FUJIFILM Corporation, Tokyo (JP)

(72) Inventor: Munetaka Kato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 237 days.

(21) Appl. No.: 17/119,575

(22) Filed: Dec. 11, 2020

(65) Prior Publication Data

US 2021/0093264 A1     Apr. 1, 2021

Related U.S. Application Data

(63) Continuation of application No. PCT/JP2019/022006, filed on Jun. 3, 2019.

(30) Foreign Application Priority Data

Jun. 22, 2018   (JP) .............................. JP2018-119355

(51) Int. Cl.
*A61B 6/00* (2006.01)
*G01T 1/20* (2006.01)

(52) U.S. Cl.
CPC .......... *A61B 6/4208* (2013.01); *G01T 1/2002* (2013.01)

(58) Field of Classification Search
None
See application file for complete search history.

(56) References Cited

U.S. PATENT DOCUMENTS

| 2008/0302970 A1* | 12/2008 | Fujieda ............. H01L 27/14663 250/370.11 |
| 2011/0114847 A1 | 5/2011 | Fujieda et al. |
| 2014/0217296 A1 | 8/2014 | Fujieda et al. |

FOREIGN PATENT DOCUMENTS

| JP | 2008-215951 A | 9/2008 |
| JP | 2010-019720 A | 1/2010 |
| JP | 2010-076438 A | 4/2010 |
| JP | 2014-081364 A | 5/2014 |
| JP | 2016-128764 A | 7/2016 |
| JP | 2017-026499 A | 2/2017 |
| JP | 2017-187424 A | 10/2017 |
| JP | 2018-009804 A | 1/2018 |

OTHER PUBLICATIONS

An Office Action; "Notice of Reasons for Refusal", mailed by the Japanese Patent Office dated May 17, 2022, which corresponds to Japanese Patent Application No. 2020-525454 and is related to U.S. Appl. No. 17/119,575; with English language translation.

(Continued)

*Primary Examiner* — Edwin C Gunberg
(74) *Attorney, Agent, or Firm* — Studebaker & Brackett PC

(57) ABSTRACT

Provided is a radiation detector having a portion in which a substrate in which a plurality of pixels for accumulating electric charges generated in accordance with light converted from radiation are formed in a pixel region, a conversion layer that converts radiation into light, a reflective pressure sensitive adhesive layer that reflects the light converted by the conversion layer, and an adhesive layer that covering a region including a region ranging from an end part of the pressure sensitive adhesive layer to a surface of the substrate are provided in this order.

13 Claims, 20 Drawing Sheets

(56) References Cited

OTHER PUBLICATIONS

An Office Action; "Notice of Reasons for Refusal," mailed by the Japanese Patent Office dated Jan. 11, 2022, which corresponds to Japanese Patent Application No. 2020-525454 and is related to U.S. Appl. No. 17/119,575 with English language translation.
International Search Report issued in PCT/JP2019/022006; dated Aug. 13, 2019.
International Preliminary Report on Patentability and Written Opinion issued in PCT/JP2019/022006; dated Dec. 22, 2020.

* cited by examiner

RADIATION DETECTOR AND RADIOGRAPHIC IMAGING APPARATUS

CROSS-REFERENCE TO RELATED APPLICATIONS

This application is a continuation application of International Application No. PCT/JP2019/022006, filed on Jun. 3, 2019, which is incorporated herein by reference in its entirety. Further, this application claims priority from Japanese Patent Application No. 2018-119355, filed on Jun. 22, 2018, the disclosure of which is incorporated by reference herein.

BACKGROUND

Technical Field

The present disclosure relates to a radiation detector and a radiographic imaging apparatus.

Related Art

In the related art, radiographic imaging apparatuses that perform radiographic imaging for medical diagnosis have been known. A radiation detector for detecting radiation transmitted through a subject and generating a radiographic image is used for such radiographic imaging apparatuses.

It is known that the radiation detector includes a substrate on which a plurality of pixels for accumulating electric charges generated in accordance with light converted from radiation are formed and a conversion layer that converts the radiation into light. In such a radiation detector, as the layer having a function of reflecting the light converted by the conversion layer, for example, a technique including a reflective layer is known (refer to Japanese Patent Application Laid-Open (JP-A) No. 2018-009804 and JP-A No. 2017-187424A)

In the above related-art radiation detector, it cannot be said that the layer having a function of reflecting light is sufficiently fixed to end parts of the substrate and the conversion layer, and there is a concern that the layer may be peeled. In particular, in a case where the substrate has flexibility, a layer having a function of reflecting light is easily peeled off due to the bending of the substrate. For that reason, a technique of fixing the layer having a function of reflecting light to the substrate and the conversion layer has been desired.

Thus, it is considered that a layer having pressure sensitive adhesiveness or the like is provided between the layer having a function of reflecting light and the conversion layer, and the layer having a function of reflecting light is fixed to the substrate and the conversion layer by the layer having pressure sensitive adhesiveness. However, in a case where the pressure sensitive adhesive layer is provided between the layer having a function of reflecting light and the conversion layer, there is a concern that the image quality of a radiographic image obtained by the radiation detector may degrade.

SUMMARY

The present disclosure provides a radiation detector and a radiographic imaging apparatus capable of suppressing the peeling of a layer having a function of reflecting light without degrading the image quality of a radiographic image as compared to a case where a layer having pressure sensitive adhesiveness is provided between the layer having a function of reflecting light and a conversion layer.

A first aspect of the present disclosure is a radiation detector including: a portion in which a substrate in which a plurality of pixels for accumulating electric charges generated in accordance with light converted from radiation are formed in a pixel region, a conversion layer that converts the radiation into light, a reflective pressure sensitive adhesive layer that reflects the light converted by the conversion layer, and an adhesive layer that covers a region including a region ranging from an end part of the pressure sensitive adhesive layer to a surface of the substrate are provided in this order.

In a second aspect of the present disclosure based on the first aspect, the pressure sensitive adhesive layer may be formed on a base material, and the pressure sensitive adhesive layer may be disposed on the conversion layer side.

In a third aspect of the present disclosure based on the second aspect, the base material may have reflectivity.

In a fourth aspect of the present disclosure based on any one of the first aspect to the third aspect, the pressure sensitive adhesive layer may be a pressure sensitive adhesive resin in which an inorganic white powder is dispersed.

According to a fifth aspect of the present disclosure based on the fourth aspect, the powder may contain at least one of titanium oxide, barium sulfate, alumina, magnesium oxide, or calcium oxide.

According to a sixth aspect of the present disclosure based on the first aspect, the pressure sensitive adhesive layer may have a laminated structure in which a reflective and metallic first pressure sensitive adhesive film and a reflective and resinous second pressure sensitive adhesive film are laminated, and the second pressure sensitive adhesive film may be disposed on the conversion layer side.

A seventh aspect of the present disclosure based on any one of the first aspect to the sixth aspect may further comprise a protective layer that covers the pressure sensitive adhesive layer and the conversion layer.

In an eighth aspect of the present disclosure based on the seventh aspect, the protective layer may have a laminated structure in which a polyethylene terephthalate film and an aluminum film are laminated.

In a ninth aspect of the present disclosure based on any one of the first aspect to the eighth aspect, a peripheral edge part of the conversion layer may have an inclination such that a thickness thereof decreases toward an outside, and an outer periphery of the pressure sensitive adhesive layer may be located at the peripheral edge part of the conversion layer.

A tenth aspect of the present disclosure is a radiation detector comprising a portion in which a substrate in which a plurality of pixels for accumulating electric charges generated in accordance with light converted from radiation are formed in a pixel region, a conversion layer that converts the radiation into light, and a reflective pressure sensitive adhesive layer that reflects the light converted by the conversion layer and covers a region including the entire conversion layer and a region ranging to the surface of the substrate are provided in this order.

In an eleventh aspect of the present disclosure based on the tenth aspect, the pressure sensitive adhesive layer may be a thermoplastic resin in which an inorganic white powder is dispersed.

In a twelfth aspect of the present disclosure based on the eleventh aspect, the powder may include at least one of titanium oxide, barium sulfate, alumina, magnesium oxide, or calcium oxide.

A thirteenth aspect of the present disclosure based on any one of the tenth aspect to the twelfth aspect may further comprise a protective layer that covers the pressure sensitive adhesive layer.

In a fourteenth aspect of the present disclosure based on the thirteenth aspect, the protective layer may have a laminated structure in which a polyethylene terephthalate film and an aluminum film are laminated.

In a fifteenth aspect of the present disclosure based on the thirteenth aspect or the fourteenth aspect, an outer periphery of the protective layer may be sealed with a sealant.

In a sixteenth aspect of the present disclosure based on any one of the seventh aspect, the eighth aspect, the thirteenth aspect, the fourteenth aspect, and the fifteenth aspect, may further comprise a reinforcing substrate provided on at least one of the protective layer side or the substrate side of a laminate including the substrate, the conversion layer, the pressure sensitive adhesive layer, and the protective layer.

In a seventeenth aspect of the present disclosure based on the sixteenth aspect, the reinforcing substrate may have higher stiffness than that of the substrate.

In an eighteenth aspect of the present disclosure based on the sixteenth aspect or the seventeenth aspect, the reinforcing substrate may have a thickness larger than that of the substrate.

In a nineteenth aspect of the present disclosure based on any one of the first aspect to the fifteenth aspect, a central region of the conversion layer may cover the pixel region of the substrate and may be larger than the pixel region of the substrate.

In a twentieth aspect of the present disclosure based on any one of the first aspect to the nineteenth aspect, a central region of the conversion layer may cover the pixel region of the substrate and may be smaller than the pixel region of the substrate.

In a twenty-first aspect of the present disclosure based on any one of the first aspect to the twentieth aspect, the substrate may have flexibility.

In a twenty-second aspect of the present disclosure based on the twenty-first aspect, the substrate may have a layer containing inorganic fine particles having an average particle diameter of 0.05 μm or more and 2.5 μm or less on a surface opposite to the conversion layer side.

In a twenty-third aspect of the present disclosure based on any one of the first aspect to the twenty-second aspect, the conversion layer may include CsI columnar crystals.

Additionally, a twenty-fourth aspect of the present disclosure is a radiation detector comprising a portion in which a substrate in which a plurality of pixels for accumulating electric charges generated in accordance with light converted from radiation are formed in a pixel region, a conversion layer that converts the radiation into light, and a protective layer that has a laminated structure in which a protective film is laminated on a reflective pressure sensitive adhesive film that covers at least the conversion layer, and covers a region including the entire conversion layer and a region ranging to a surface of the substrate are provided in this order, and the pressure sensitive adhesive film of the protective layer is disposed on the conversion layer side.

Additionally, a twenty-fifth aspect of the present disclosure is a radiographic imaging apparatus comprising the radiation detector according to any one of the first aspect to the twenty-fourth aspects; a control unit that outputs a control signal for reading out electric charges accumulated in the plurality of pixels; a drive unit that reads out the electric charges from the plurality of pixels in accordance with the control signal; and a signal processing unit that receives electrical signals according to the electric charges read from the plurality of pixels input thereto and generates image data according to the received electric signals to output the image data to the control unit.

According to the above aspects, the radiation detector and the radiographic imaging apparatus of the present disclosure can suppress the peeling of the layer having a function of reflecting light without degrading the image quality of the radiographic image as compared to the case where the layer having pressure sensitive adhesiveness is provided between the layer having a function of reflecting light and the conversion layer.

DESCRIPTION OF EMBODIMENTS

Figure 1:
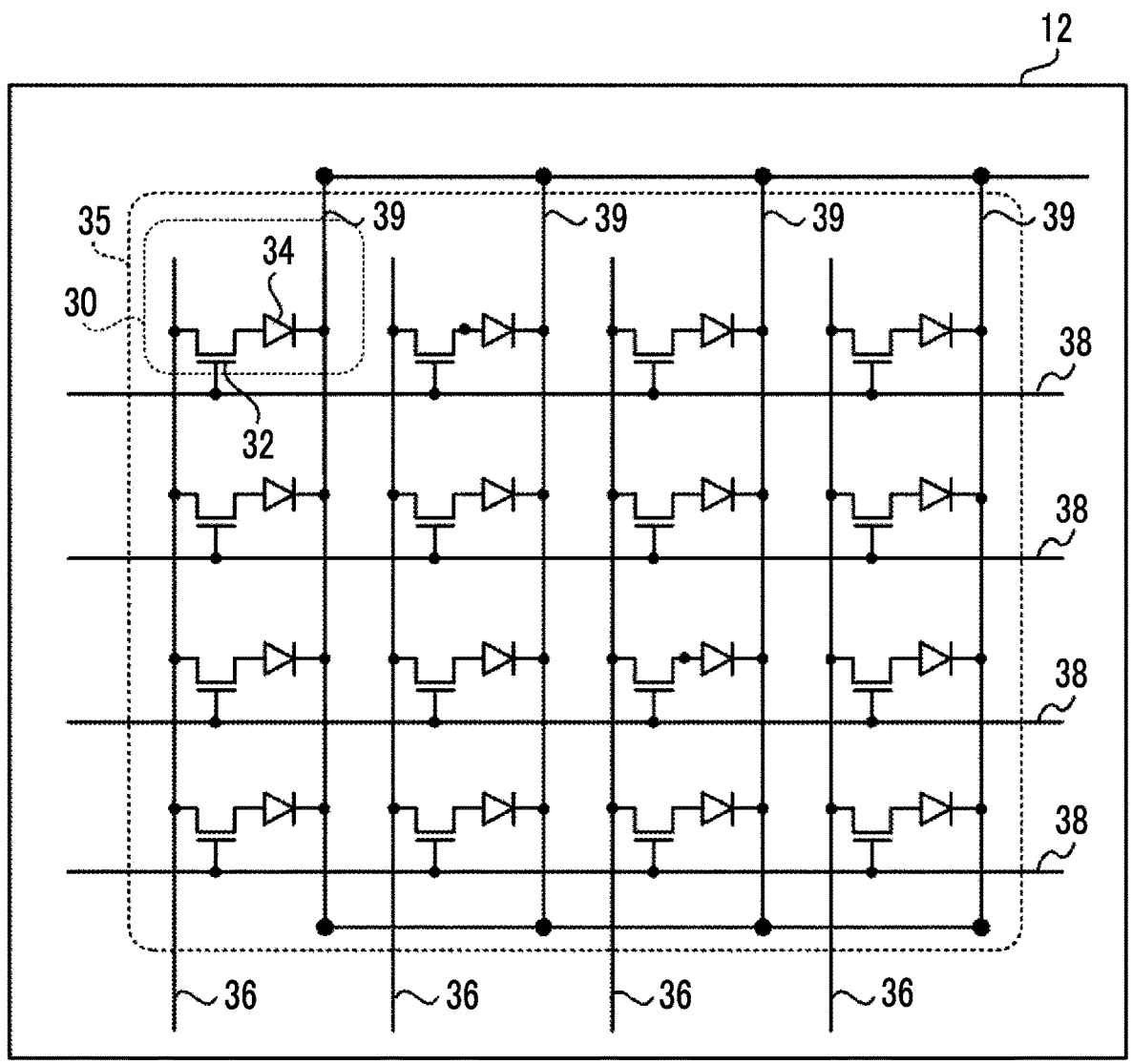
FIG. 1 is a configuration diagram illustrating an example of a configuration of a thin film transistor (TFT) substrate in a radiation detector according to a first exemplary embodiment.

Hereinafter, exemplary embodiments of the present disclosure will be described in detail with reference to the drawings. In addition, the present exemplary embodiments do not limit the present disclosure.

First Exemplary Embodiment

A radiation detector of the present exemplary embodiment has a function of detecting radiation transmitted through a subject to output image information representing a radiographic image of the subject. The radiation detector of the present exemplary embodiment comprises a thin film transistor (TFT) substrate, and a conversion layer that converts radiation into light (refer to a TFT substrate 12 and a conversion layer 14 of a radiation detector 10 in FIG. 3).

First, an example of the configuration of the TFT substrate 12 in the radiation detector of the present exemplary embodiment will be described with reference to FIG. 1. In addition, the TFT substrate 12 of the present exemplary embodiment is a substrate in which a pixel array 31 including a plurality of pixels 30 is formed in a pixel region 35 of a base material 11. Therefore, in the following description, the expression "the pixel region 35" is used as the same meaning as "the pixel array 31". The TFT substrate 12 of the present exemplary embodiment is an example of a substrate of the disclosed technique.

The base material 11 is, for example, a glass substrate, such as alkali-free glass, a resin sheet including plastic, such as polyimide, or the like. A specific example of the resin sheet is XENOMAX (registered trademark). Additionally, the base material 11 preferably have flexibility. In this case, the above resin sheet, a relatively thin glass substrate, or the like is preferable as the base material 11.

The thickness of the base material 11 may be a thickness in which desired flexibility is obtained in accordance with the hardness of the material, the size of the TFT substrate 12, and the like. For example, in a case where the base material 11 is a resin sheet, the thickness thereof may be 5 μm to 125 μm and more preferably 20 μm to 50 μm. Additionally, for example, in a case where the base material 11 is a glass substrate, in general, in a case where the size of one side is about 43 cm and the thickness is 0.3 mm or less, the base material 11 has flexibility, and tends to bend similarly to the base material 11 made of resin. Therefore, the thickness may be 0.3 mm or less.

In addition, it is preferable that the base material 11 has properties that, in a state where the coefficient of thermal expansion at 300° C. to 400° C. is 20 ppm/K or less and the thickness is 25 μm, the percentage of thermal shrinkage in a machine direction (MD) at 400° C. is 0.5% or less and the modulus of elasticity at 500° C. is 1 GPa or more. A specific example of the resin sheet having such properties may include the above XENOMAX (registered trademark) having a layer containing inorganic fine particles having an average particle diameter of 0.05 μm or more and 2.5 μm or less is provided on the surface opposite to the side on which the conversion layer 14 is provided.

In addition, evaluation methods described in JP2010-076438A are applied as methods of measuring the thickness, the coefficient of thermal expansion, the modulus of elasticity, the average particle diameter, and the like in the present exemplary embodiment. For example, a method of measuring the coefficient of thermal expansion is to measure the ratio of expansion and contraction in the machine direction (MD) and a transverse direction (TD) under the following conditions, measure the ratio of expansion and contraction and temperature at intervals of 10° C., such as 90° C. to 100° C. and 100° C. to 110° C., perform this measurement up to 400° C., and convert the coefficient of thermal expansion (ppm/° C.) derived as an average value of all measured values from 100° C. to 350° C. into a coefficient of thermal expansion in units of ppm/K. As the measurement conditions of the coefficient of thermal expansion, the TMA4000S apparatus manufactured by MAC SCIENCE CO., LTD. was used, the sample length was 10 mm, the sample width was 2 mm, the initial load was 34.5 g/mm$^2$, the temperature rising start temperature was 25° C., the temperature rising end temperature was 400° C., the temperature rising rate was 5° C./min, and the atmosphere was argon.

Each of the pixels 30 includes a sensor unit 34 that generates and accumulates electric charges in accordance with the light converted by the conversion layer, and a switching element 32 that reads out the electric charges accumulated by the sensor unit 34. In the present exemplary embodiment, as an example, a thin film transistor (TFT) is used as the switching element 32. For that reason, in the following description, the switching element 32 is referred to as a "TFT 32".

The plurality of pixels 30 are two-dimensionally disposed in one direction (a scanning wiring direction corresponding to a transverse direction of FIG. 1, hereinafter referred to as a "row direction"), and a direction (a signal wiring direction corresponding to a longitudinal direction of FIG. 1, hereinafter referred as a "column direction") crossing the row direction in the pixel region 35 of the TFT substrate 12. Although an array of the pixels 30 is illustrated in a simplified manner in FIG. 1, for example, 1024×1024 pixels 30 are disposed in the row direction and the column direction.

Additionally, a plurality of scanning wiring lines 38 for controlling switching states (ON and OFF) of the TFTs 32, and a plurality of signal wiring lines 36, which are provided for respective columns of the pixels 30 and from which electric charges accumulated in the sensor units 34 are read, are provided in a mutually intersecting manner in the radiation detector 10. The plurality of scanning wiring lines 38 are respectively connected to a drive unit (refer to a drive unit 103 in FIGS. 22 and 23) outside the radiation detector 10 via pads (not illustrated), respectively, provided in the TFT substrate 12, and thereby, control signals, which are output from the drive unit to control the switching states of the TFTs 32, flow to the plurality of scanning wiring lines 38, respectively. Additionally, the plurality of signal wiring lines 36 are respectively connected to a signal processing unit (refer to a signal processing unit 104 in FIGS. 22 and 23) outside the radiation detector 10 via pads (not illustrated), respectively, provided in the TFT substrate 12, and thereby, electric charges read from the respective pixels 30 are output to the signal processing unit.

Additionally, common wiring lines 39 are provided in a wiring direction of the signal wiring lines 36 at the sensor units 34 of the respective pixels 30 in order to apply bias voltages to the respective pixels 30. Bias voltages are applied to the respective pixels 30 from a bias power source by connecting the common wiring lines 39 to the bias power source outside the radiation detector 10 via pads (not illustrated) provided in the TFT substrate 12.

Figure 2:
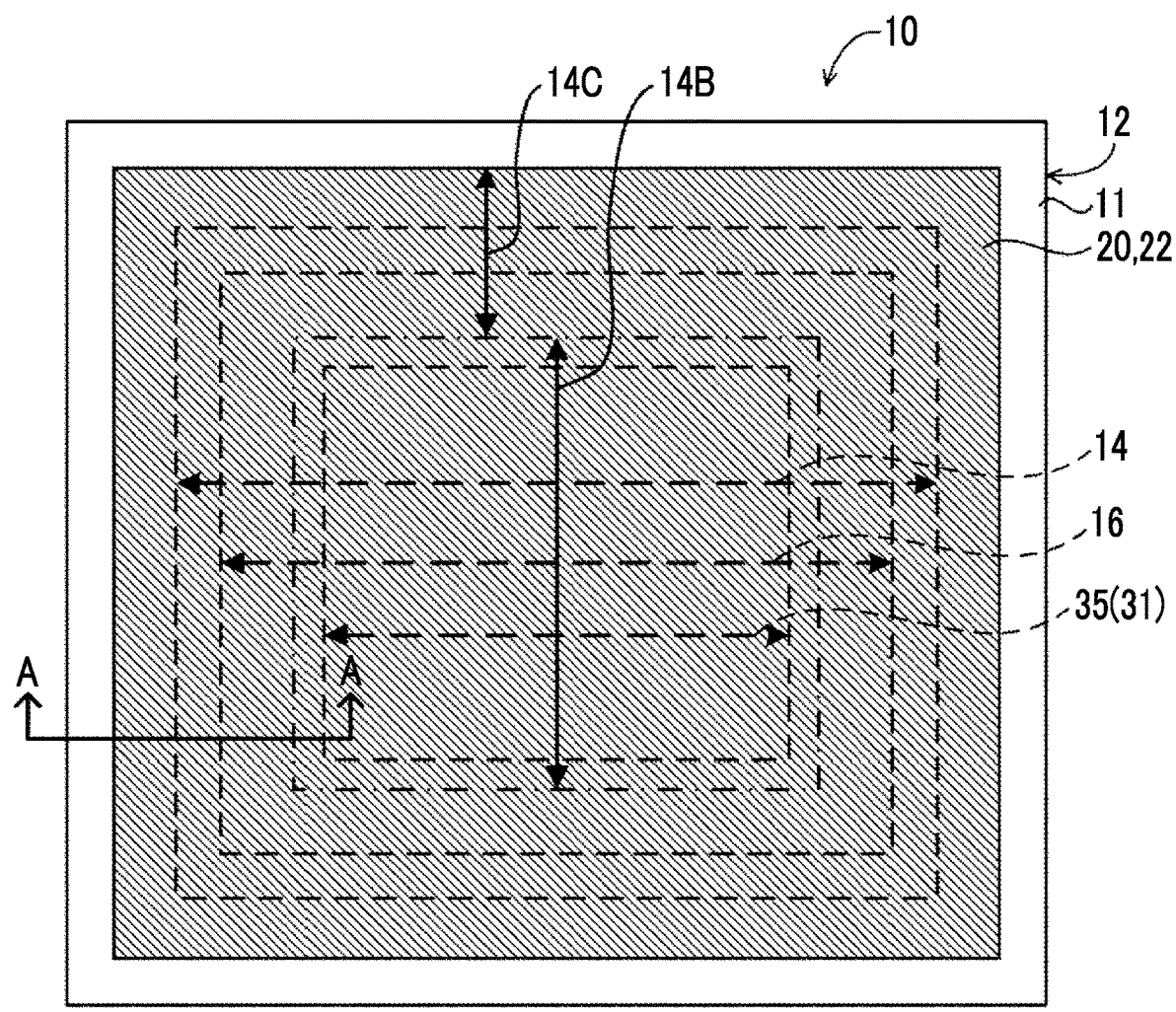
FIG. 2 is a plan view of an example of a radiation detector of a first exemplary embodiment as seen from the side on which a conversion layer is provided.
Figure 3:
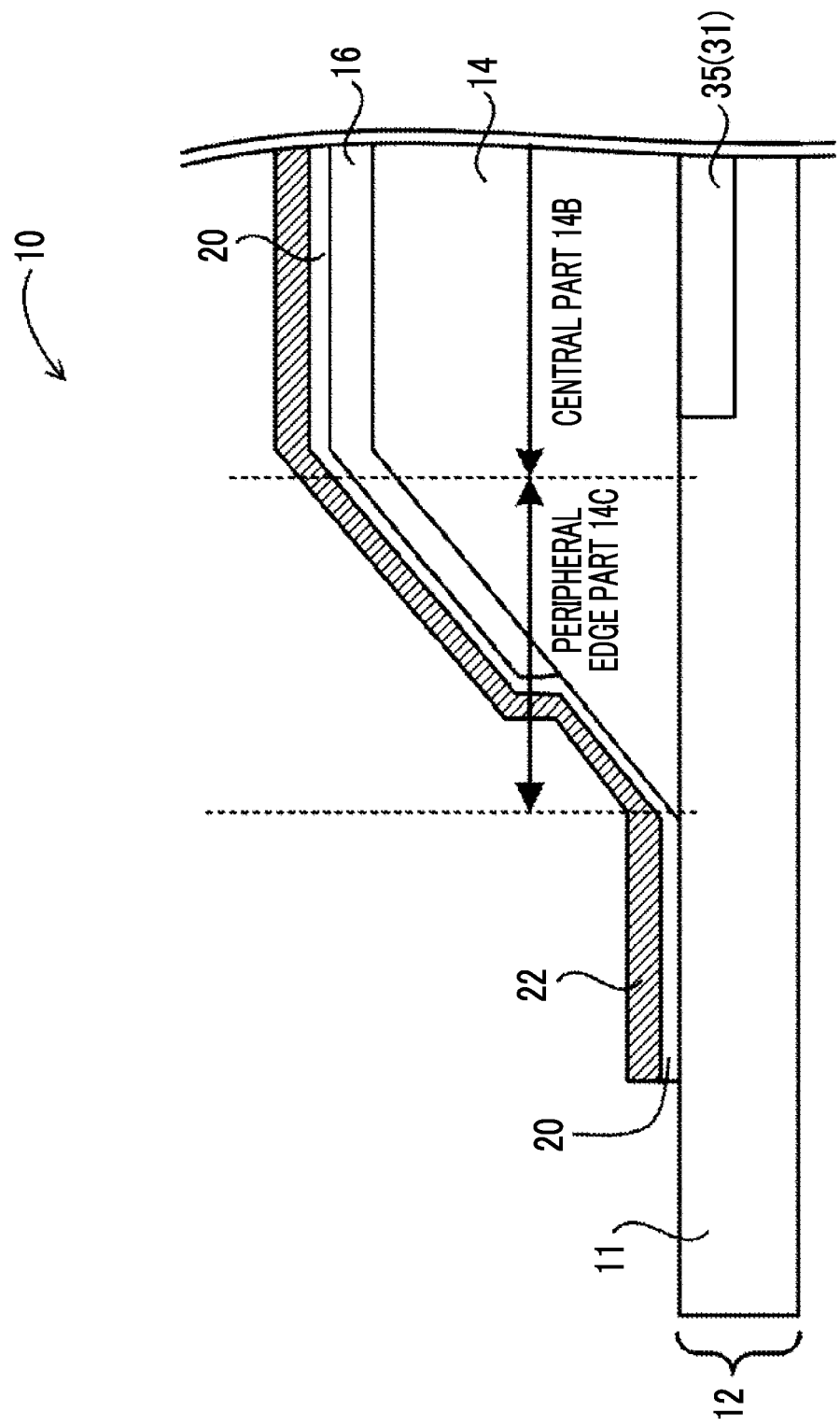
FIG. 3 is a cross-sectional view taken along line A-A of the radiation detector illustrated in FIG. 2.

In the radiation detector 10 of the present exemplary embodiment, the conversion layer 14 is formed on the TFT substrate 12. FIG. 2 is a plan view of the radiation detector 10 of the present exemplary embodiment as seen from the side on which the conversion layer 14 is formed. Additionally, FIG. 3 is a cross-sectional view taken along line A-A of the radiation detector 10 in FIG. 2. In addition, in the following description, the term "on" in the structure of the radiation detector 10 means "on" in a positional relationship with reference to the TFT substrate 12 side.

As illustrated in FIGS. 2 and 3, the conversion layer 14 of the present exemplary embodiment is provided on a partial region including the pixel region 35 of the TFT substrate 12. In this way, the conversion layer 14 of the present exemplary embodiment is not provided on the region of an outer peripheral part of the TFT substrate 12.

In the present exemplary embodiment, a scintillator including CsI (cesium iodide) is used as an example of the conversion layer 14. It is preferable that such a scintillator includes, for example, CsI:Tl (cesium iodide to which thallium is added) or CsI:Na (cesium iodide to which sodium is added) having an emission spectrum of 400 nm to 700 nm at the time of X-ray radiation. In addition, the emission peak wavelength in a visible light region of CsI:Tl is 565 nm.

Figure 5:
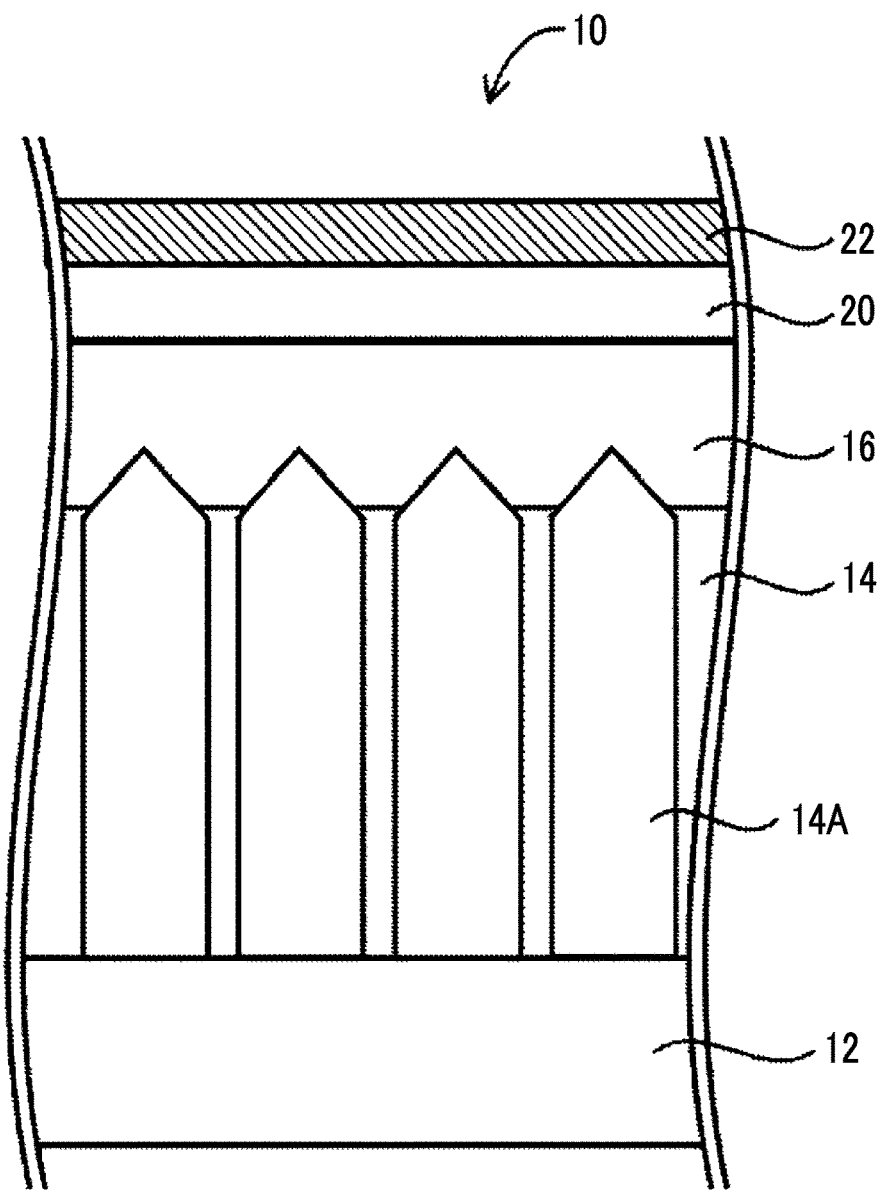
FIG. 5 is a cross-sectional view illustrating an example of a laminated state of a TFT substrate, the conversion layer, a pressure sensitive adhesive layer, an adhesive layer, and a protective layer in the radiation detector of the first exemplary embodiment.

In the radiation detector 10 of the present exemplary embodiment, as in an example illustrated in FIG. 5, the conversion layer 14 is directly formed on the TFT substrate 12 as strip-shaped columnar crystals 14A by vapor-phase deposition methods, such as a vacuum vapor deposition method, a sputtering method, and a chemical vapor deposition (CVD) method. For example, in a case where CsI:Tl is used as the conversion layer 14, a vacuum vapor deposition method is used as a method of forming the conversion layer 14. In the vacuum vapor deposition method, CsI:Tl is heated and gasified by heating means, such as a resistance heating-type crucible in an environment with the vacuum degree of 0.01 Pa to 10 Pa, and CsI:Tl is deposited on the TFT substrate 12 with the temperature of the TFT substrate 12 as the room temperature (20° C.) to 300° C. As the thickness of the conversion layer 14, 100 μm to 800 μm is preferable.

In addition, in the present exemplary embodiment, end parts of columnar crystals 14A of the conversion layer 14 on a base point side (a TFT substrate 12 side in the present embodiment) in a growth direction are referred to as "roots", and sharpened end parts opposite to the roots in the growth direction are referred to as "tips".

Figure 4:
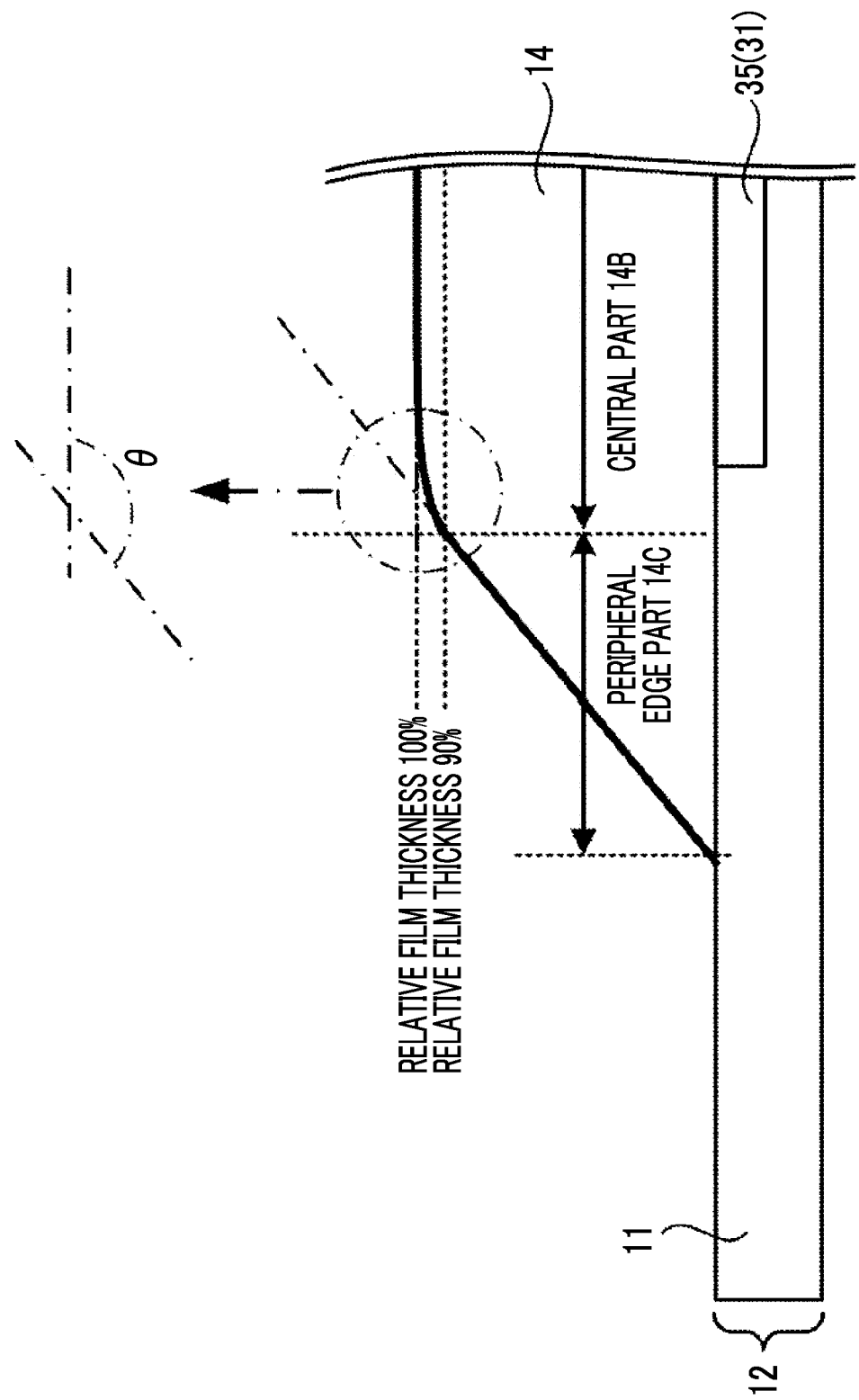
FIG. 4 is a cross-sectional view for explaining a peripheral edge part and a central part in the conversion layer of the present exemplary embodiment.

Additionally, since the conversion layer 14 of the present exemplary embodiment is formed by the vapor-phase deposition methods as described above, as illustrated in FIG. 3, the thickness of the outer peripheral region of the conversion layer 14 tends to decrease toward the outside as viewed as a whole. For that reason, the conversion layer 14 has an inclination such that the thickness thereof decreases toward the outside. In the present exemplary embodiment, an average value of thicknesses of the conversion layer 14, which are regarded as being substantially constant in a case where a manufacturing error and a measurement error is neglected and are within a predetermined range from the center of the conversion layer 14, is adopted as a reference, and as illustrated in FIG. 4, as an example, an outer peripheral region where a relative film thickness (hereinafter referred to as "relative film thickness") to a reference thickness is 90% or less is referred to as a "peripheral edge part (peripheral edge part 14C)". Additionally, as illustrated in FIG. 4, the region of the conversion layer 14 surrounded by the peripheral edge part 14C is referred to as a "central part (central part 14B)". In other words, the "central part" means a region that includes at least a portion in which the thickness of the conversion layer 14 is substantially constant and that also includes a portion in which the relative film thickness exceeds 90%. In addition, in the present exemplary embodiment, as illustrated in FIGS. 2 and 3, the pixel region 35 is smaller than the central part 14B, and the pixel region 35 is covered with the central part 14B.

In the present exemplary embodiment, as a specific example, an outer peripheral region, which is within a region of less than 5 mm from the outer periphery of the conversion layer 14 and has a relative film thickness of 90% or less, is referred to as a "peripheral edge part (peripheral edge part 14C)". For that reason, as illustrated in FIG. 3, FIG. 4, and the like, in the peripheral edge part 14C, the thickness of the conversion layer 14 tends to gradually decrease toward the outer periphery (edge).

In addition, in the present exemplary embodiment, as an example in which the thickness of the conversion layer 14 decreases toward the outer periphery, a form in which the conversion layer 14 has a constant inclination angle of θ and the thickness gradually decreases is exemplified. However, the form of the conversion layer is not limited this form and may be, for example, a form in which the thickness changes stepwise.

In addition, the method of measuring the inclination angle θ is not particularly limited. However, in the present exemplary embodiment, as an example, in the method of measuring the inclination angle θ, portions of an end part of the conversion layer 14 were peeled from the TFT substrate 12 at the positions of four spots with regular intervals at one side of a rectangular conversion layer 14 and were obtained as respective samples. Measurement was performed by observing the four samples using an optical microscope after the four samples were polished and sectioned. An average value of measured values of the four samples was set as the inclination angle θ at the side of the conversion layer 14 where the samples were prepared.

Figure 6:
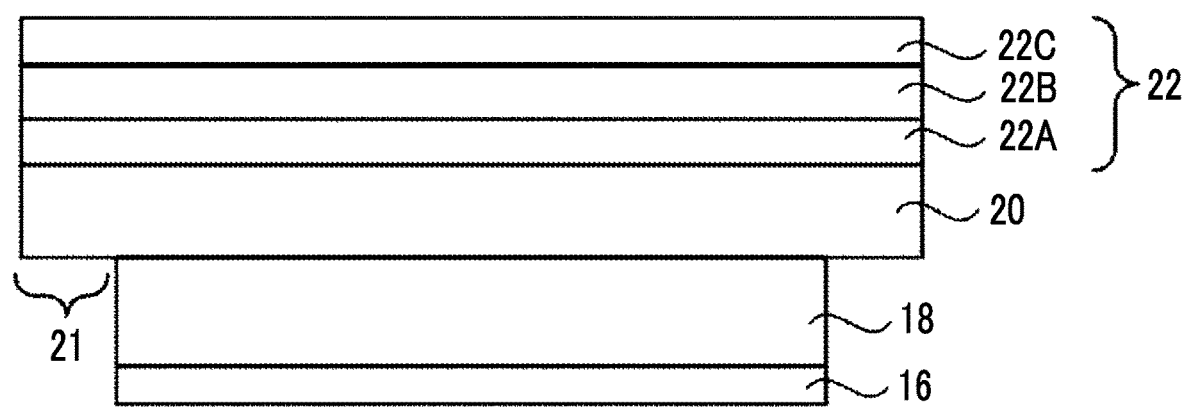
FIG. 6 is a cross-sectional view schematically illustrating a cross-section of an example of a pressure sensitive adhesive layer, an adhesive layer, and a protective layer according to first to third exemplary embodiments.

Moreover, as illustrated in FIGS. 2 to 6, the radiation detector 10 of the present exemplary embodiment comprises a pressure sensitive adhesive layer 16, an adhesive layer 20, and a protective layer 22. FIG. 6 illustrates a cross-sectional view schematically illustrating a cross-section of an example of the pressure sensitive adhesive layer 16, the adhesive layer 20, and the protective layer 22 of the present exemplary embodiment.

As illustrated in FIGS. 2 and 3 as an example, the pressure sensitive adhesive layer 16 is provided on a region including a portion of the peripheral edge part 14C and the entire central part 14B in the conversion layer 14. In other words, the pressure sensitive adhesive layer 16 covers the central part 14B and a portion of the peripheral edge part 14C in the conversion layer 14. Additionally, as illustrated in FIG. 5, in the radiation detector 10 of the present exemplary embodiment, the tip of the conversion layer 14 enters the pressure sensitive adhesive layer 16.

The pressure sensitive adhesive layer 16 of the present exemplary embodiment is a reflective pressure sensitive adhesive layer that reflects the light converted by the conversion layer 14. In the present exemplary embodiment, as an example of the pressure sensitive adhesive layer 16, a white pressure sensitive adhesive layer in which an inorganic white powder is dispersed in a pressure sensitive adhesive resin is used. In addition, in the present exemplary embodiment, "white" means a state where visible light of all wavelengths is diffusely reflected and is referred to as a "mirror surface" in a case where light is reflected with directivity. Additionally, the "reflectivity" of the pressure sensitive adhesive layer 16 or the like that reflects light means a state where the average reflectance of light of 500 nm to 550 nm is 80% or more.

Additionally, the "pressure sensitive adhesive layer" and the "adhesive layer" have a function of making direct contact layers, in the present exemplary embodiment, the conversion layer 14 and the base material 18 (refer to FIG. 6) difficult to separate from the pressure sensitive adhesive layer 16. Additionally, the "pressure sensitive adhesive layer" and the "adhesive layer" are layers having a state of being bonded to a solid surface by a certain force not limited to chemical bonding.

Examples of the pressure sensitive adhesive resin include acrylic glue. Examples of the inorganic white powder include powders containing at least one of titanium oxide ($TiO_2$), barium sulfate ($BaSO_4$), alumina ($Al_2O_3$), magnesium oxide (MgO), and calcium oxide (CaO). As an example, in the present exemplary embodiment, a white pressure sensitive adhesive layer is obtained by dispersing white powder as a filler in a transparent glue (resin).

As illustrated in FIG. 6, the pressure sensitive adhesive layer 16 of the present exemplary embodiment is formed on the base material 18, the base material 18 is disposed on the adhesive layer 20 side, and the pressure sensitive adhesive layer 16 is disposed on the conversion layer 14 (not illustrated in FIG. 6) side. Examples of the material of the base material 18 include reflective white polyethylene terephthalate (PET) that reflects light. Not limited to the present exemplary embodiment, the base material 18 may not have reflectivity. Specifically, a material that does not reflect the light converted by the conversion layer 14, for example, a light transmissive material may be used. However, it is preferable to use a reflective material as in the present exemplary embodiment. In this case, since the light that could not be completely reflected (leaked) by the pressure sensitive adhesive layer 16 can be reflected by the base material 18, the reflectance of the pressure sensitive adhesive layer 16 and the base material 18 as a whole can be improved.

In addition, the white PET is obtained by adding a white pigment, such as $TiO_2$ or barium sulfate, to PET. Additionally, the polyester-based high-reflection sheet is a sheet (film) having a multilayer structure in which a plurality of thin polyester sheets are laminated. Additionally, the foamed white PET is a white PET of which the surface is porous.

In addition, in a case where the combined thickness of the pressure sensitive adhesive layer 16 and the base material 18 increases, the step between an upper surface of an outer peripheral part of the pressure sensitive adhesive layer 16 and the base material 18 and an upper surface of the conversion layer 14 increases. In a case where the step is large and in a case where the pressure sensitive adhesive layer 16 having the protective layer 22 bonded to the TFT substrate 12 on which the conversion layer 14 is formed, there is a case where the protective layer 22 is lifted up at the step portion. Additionally, in a case where the combined thickness of the pressure sensitive adhesive layer 16 and the base material 18 increases, a so-called stiffness state is brought about. Therefore, there is a case where bending does not occur easily along the inclination of the peripheral edge part 14C of the conversion layer 14 and is not easily processed. On the other hand, as the thickness of the pressure sensitive adhesive layer 16 decreases, reflectance decreases. In a case where the reflectance decreases, the image quality of a radiographic image to be obtained by the radiation detector 10 also tends to deteriorate. For that reason, it is preferable that the thicknesses of the pressure sensitive adhesive layer 16 and the base material 18 are determined from a desired reflectance (for example, 80%) based on the viewpoint of the image quality of a radiographic image obtained by the radiation detector 10 and from the viewpoint of manufacturing and processing.

As illustrated in FIGS. 2 and 3 as an example, the adhesive layer 20 covers a region including a region ranging from an end part of the pressure sensitive adhesive layer 16 to the surface of the TFT substrate 12, and specifically, covers the entire conversion layer 14 on which the pressure sensitive adhesive layer 16 is provided, and a portion of the surface of the TFT substrate 12. In other words, in the radiation detector 10 of the present exemplary embodiment, the adhesive layer 20 that covers the entire conversion layer 14 in which the pressure sensitive adhesive layer 16 is provided is directly fixed (adhered) to a portion of the surface of the TFT substrate 12. The adhesive layer 20 has a function of fixing the pressure sensitive adhesive layer 16 and the protective layer 22 to the TFT substrate 12 and the conversion layer 14. Examples of the material of the adhesive layer 20 include acrylic pressure sensitive adhesives, hot-melt pressure sensitive adhesives, and silicone adhesives. Examples of the acrylic pressure sensitive adhesive include urethane acrylate, acrylic resin acrylate, epoxy acrylate, and the like. Examples of the hot-melt pressure sensitive adhesive include thermoplastics, such as ethylene-vinyl acetate copolymer resin (EVA), ethylene-acrylate copolymer resin (EAA), ethylene-ethyl acrylate copolymer resin (EEA), and ethylene-methyl methacrylate copolymer (EMMA). In addition, in the present exemplary embodiment, the adhesive force of the adhesive layer 20 is stronger than the adhesive force of the pressure sensitive adhesive layer 16.

Moreover, as illustrated in FIGS. 2 and 3 as an example, the protective layer 22 is provided on the adhesive layer 20. The protective layer 22 of the present exemplary embodiment has a function of protecting the conversion layer 14 from moisture, such as humidity. Additionally, the protective layer 22 of the present exemplary embodiment has a function of fixing the pressure sensitive adhesive layer 16 to the TFT substrate 12 and the conversion layer 14 together with the adhesive layer 20. Examples of the material of the protective layer 22 include an organic film, and specifically, a single film or a laminated film made of PET, polyphenylene sulfide (PPS), oriented polypropylene (OPP), polyethylene naphthalate (PEN), polyimide (PI), and the like. Additionally, as the protective layer 22, an ALPET (registered trademark) sheet obtained by laminating aluminum, for example by causing aluminum foil to adhere to an insulating sheet (film), such as PET may be used. In the present exemplary embodiment, as an example, as illustrated in FIG. 6, the protective layer 22 is a laminated film in which a PET film 22A, an aluminum foil film 22B, and a PET film 22C are laminated.

An example of a method of manufacturing the radiation detector 10 of the present exemplary embodiment illustrated in FIGS. 2 to 6 includes the following method.

The pressure sensitive adhesive layer 16 is applied to the base material 18 having a desired size that matches the radiation detector 10 In advance. The protective layer 22 is applied to the adhesive layer 20 having a desired size that matches the radiation detector 10. Then, the base material 18 coated with the pressure sensitive adhesive layer 16 and the protective layer 22 coated with the adhesive layer 20 are bonded together to prepare a laminated film in the state illustrated in FIG. 6. In the present exemplary embodiment, as illustrated in FIG. 6, the base material 18 and the pressure sensitive adhesive layer 16 are smaller than the adhesive layer 20 and the protective layer 22, and an adhesive part 21 is provided around the base material 18 and the pressure sensitive adhesive layer 16.

Meanwhile, the conversion layer 14 is formed directly on the TFT substrate 12, by the vapor-phase deposition methods as described above.

Then, the laminated film is disposed on the TFT substrate 12 on which the conversion layer 14 is formed so as to cover the entire conversion layer 14, and the adhesive part 21 is bonded to the TFT substrate 12, thereby sealing the conversion layer 14. In addition, in a case where the above bonding is performed, the bonding is performed under the atmospheric pressure or under reduced pressure (under vacuum). However, in order to suppress entry of air or the like while being bonded to each other, it is preferable to perform the bonding under reduced pressure.

Figure 7:
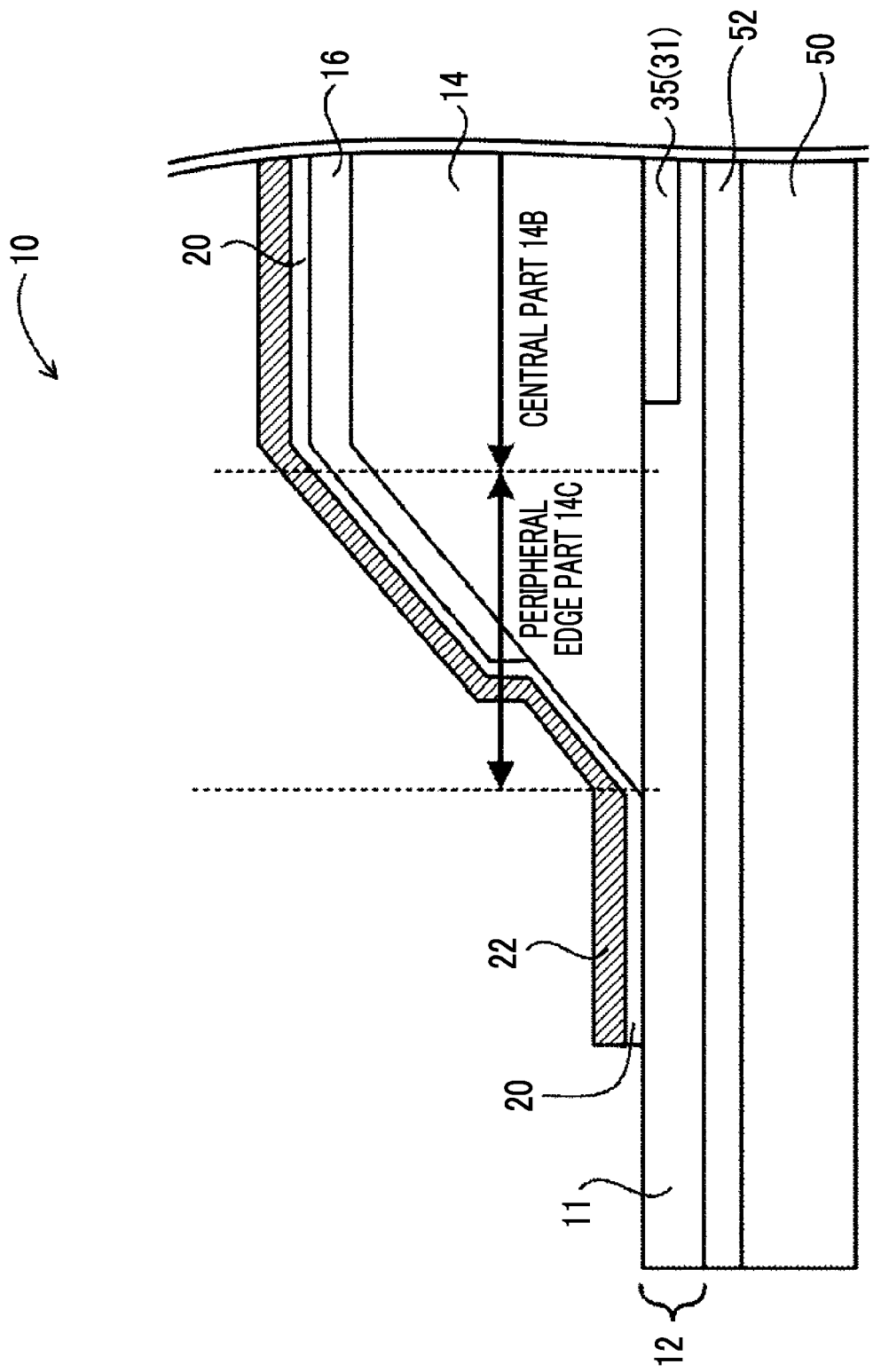
FIG. 7 is a view illustrating an example of a method of manufacturing the radiation detector of the first exemplary embodiment.

In addition, in the radiation detector 10 of the present exemplary embodiment illustrated in FIGS. 2 to 6, in the case of a glass substrate in which the thickness of the base material 11 is relatively small, the conversion layer 14, the pressure sensitive adhesive layer 16, the adhesive layer 20, and the protective layer 22 may be sequentially formed on the TFT substrate 12 as described above. Meanwhile, in a case where the base material 11 is a relatively thin substrate, for example, a substrate having flexibility, as in an example illustrated in FIG. 7, the TFT substrate 12 is formed on a support body 50, such as a glass substrate having a thickness larger than the base material 11, via a peeling layer 52, for example by a lamination method or the like. Moreover, similarly to the above, the TFT substrate 12 is peeled from the support body 50 by the peeling layer 52 after the conversion layer 14, the pressure sensitive adhesive layer 16, the adhesive layer 20, and the protective layer 22 are sequentially formed. The peeling method is not particularly limited. For example, in a mechanical lamination method, any of the four sides of the TFT substrate 12 (base material 11) may be used as a starting point for peeling and the TFT substrate 12 may be gradually peeled off from the support body 50 toward an opposite side from the side to be the starting point. Additionally, for example, in a laser peeling (laser lift-off) method, the TFT substrate 12 may be peeled from the support 50 by radiating a laser beam from a back surface (a surface opposite to the surface on which the TFT substrate 12 is provided) of the support 50 and by decomposing the peeling layer 52 with the laser beam transmitted through the support body 50.

In this way, in the radiation detector 10 according to the present exemplary embodiment, the adhesive layer 20 and the protective layer 22 cover the entire pressure sensitive adhesive layer 16. Additionally, the adhesive layer 20 and the protective layer 22 are directly fixed onto the TFT substrate 12.

In order to collect (reflect) more light converted by the conversion layer 14 on the TFT substrate 12, the pressure sensitive adhesive layer 16 having a function of reflecting light also covers the peripheral edge part 14C of the conversion layer 14, so that the pressure sensitive adhesive layer 16 easily tends to be peeled off from the conversion layer 14 at the inclined peripheral edge part 14C. Additionally, in a case where the base material 11 of the TFT substrate 12 has flexibility, the pressure sensitive adhesive layer 16 tends to be easily peeled off from the conversion layer 14 due to the bending of the TFT substrate 12.

In contrast, according to the radiation detector 10 of the present exemplary embodiment, by virtue of the above configuration, the peeling of the pressure sensitive adhesive layer 16 is suppressed, and even in a case where the TFT substrate 12 has flexibility, the peeling of the pressure sensitive adhesive layer 16 is suppressed.

Additionally, according to the radiation detector 10 of the present exemplary embodiment, the pressure sensitive adhesive layer 16 has both functions of a layer having a function of reflecting light and a layer having pressure sensitive adhesiveness. Therefore, the thickness of the pressure sensitive adhesive layer can be made larger than in a case where the respective layers are formed as separated layers. Therefore, according to the radiation detector 10 of the present exemplary embodiment, since the pressure sensitive adhesive force can be increased, the pressure sensitive adhesive layer 16 is less likely to peel off.

Figure 8:
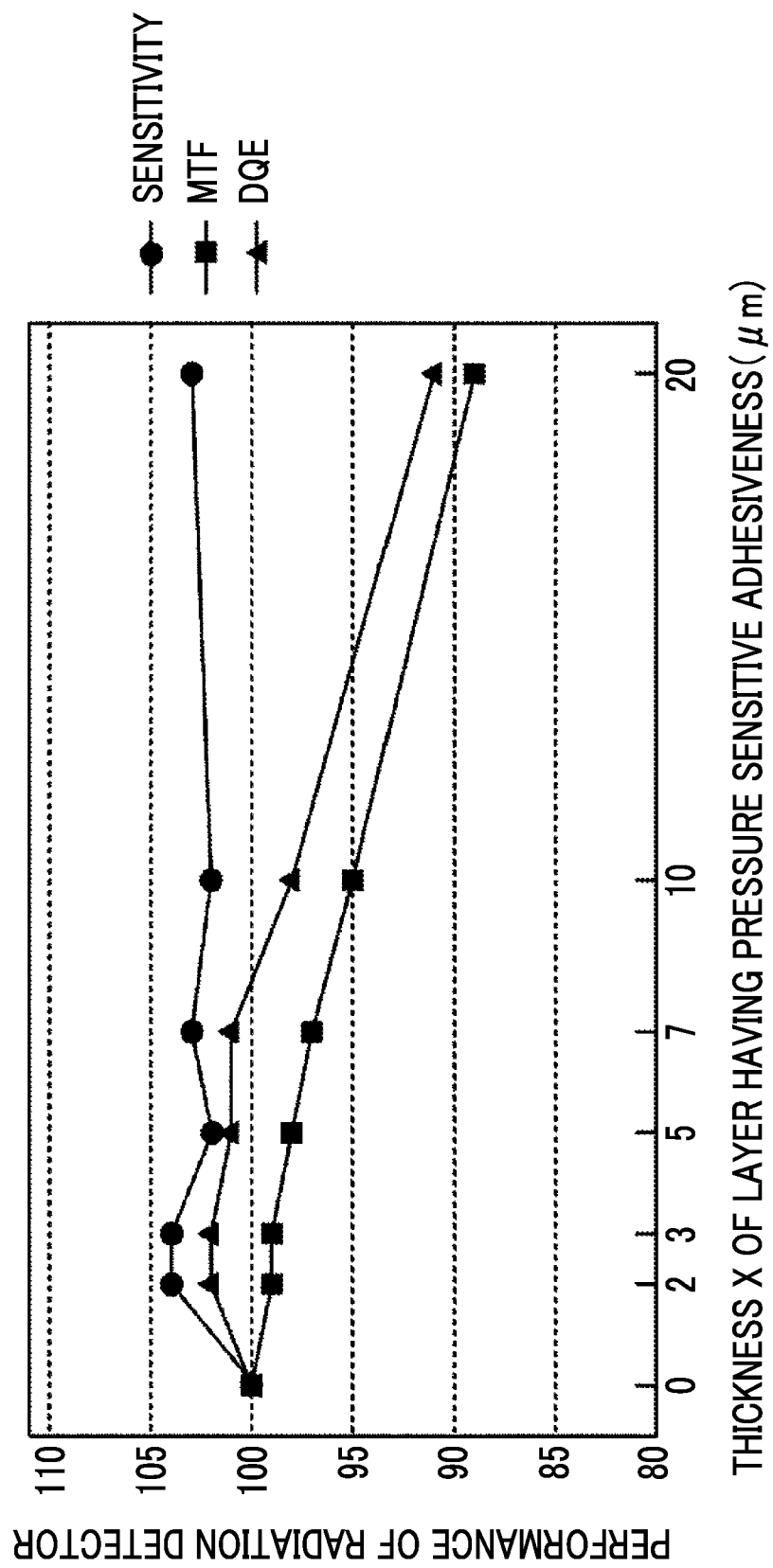
FIG. 8 is a graph illustrating an example of a correspondence relationship between the thickness of a layer having pressure sensitive adhesiveness and the performance of a radiation detector.

Additionally, in the present disclosure, it has been found that there is a relationship between the interval between the conversion layer 14 and the layer having a function of reflecting light (the pressure sensitive adhesive layer 16 in the present exemplary embodiment) and the performance related to the image quality of the radiographic image obtained by the radiation detector 10 (hereinafter, simply referred to as the "performance" of the radiation detector). Unlike the present exemplary embodiment, a radiation detector having a form in which a layer having pressure sensitive adhesiveness is provided between the conversion layer 14 and a layer having a function of reflecting light, and the layer having a function of reflecting light is fixed, in other words, a radiation detector in which, unlike the pressure sensitive adhesive layer 16 of the present exemplary embodiment, a layer having reflectivity and the layer having pressure sensitive adhesiveness are separately provided will be taken as an example, and the above relationship will be described with reference to FIG. 8. FIG. 8 is a graph illustrating an example of a correspondence relationship between the thickness X of the transparent pressure sensitive adhesive layer and the performance of the radiation detector.

In the correspondence relationship illustrated in FIG. 8, sensitivity, modulation transfer function (MTF), and detective quantum efficiency (DQE) are evaluated as the performance of the radiation detector 10. Additionally, the performance was measured with the quality of radiation being based on IEC62220-1 of International Electrotechnical Commission (IEC) standard, under the RQA5 conditions, and with the radiation dose (absorbed dose) as 2.5 µGy, and was evaluated as a relative value with the measured value obtained by a radiation detector of a comparative example being 100 in a case where only the layer having a function of reflecting light was provided (the layer having pressure sensitive adhesiveness was not provided).

Additionally, for the measurement of the performance, a laminated film in which a radiation detector obtained by laminating the transparent pressure sensitive adhesive layer, the layer having a function of reflecting light, the base material 18, the adhesive layer 20, and the protective layer 22 were bonded was used with respect to a radiation detector in a state in which the conversion layer 14 using CsI was formed on the TFT substrate 12 including the pixels 30 having a size of 150 μm square. Since a sheet cut out from a roll-shaped pressure sensitive adhesive sheet having a length of 100 m was used as a sheet for the layer having pressure sensitive adhesiveness, the thickness of the layer having pressure sensitive adhesiveness was obtained by measuring the thicknesses at three different positions (total of 6 positions) in the width direction at each of the beginning and the end of the roll using a scanning electron microscope (SEM) and taking an average value of the measured values as the thickness X of the pressure sensitive adhesive layer. Additionally, a layer in which an acrylic pressure sensitive adhesive was used as the material was used as the layer having pressure sensitive adhesiveness. In addition, even in a case where a layer in which the hot-melt pressure sensitive adhesive was used as the material was used as the layer having pressure sensitive adhesiveness, the same tendency as in FIG. 8 was obtained for the correspondence relationship between the thickness X of the layer having pressure sensitive adhesiveness and the performance of the radiation detector.

As the thickness X of the layer having pressure sensitive adhesiveness increases (that is, as the interval between the conversion layer 14 and the layer having the function of reflecting light increases), the light converted by the conversion layer 14 is blurred within the layer having pressure sensitive adhesiveness. Therefore, the radiographic image obtained by the radiation detector 10 becomes a blurred image as a result. For that reason, as illustrated in FIG. 8, as the thickness X of the layer having pressure sensitive adhesiveness increases, the MTF and DQE decrease, and the degree of decrease also increases.

In this way, from the viewpoint of suppressing the blurring of light described above, it is preferable that the interval between the conversion layer 14 and the layer having the function of reflecting light is narrow. In the radiation detector 10 of the present exemplary embodiment, the reflective pressure sensitive adhesive layer 16 having the function of reflecting light is directly formed on the conversion layer 14. For that reason, according to the radiation detector 10 of the present exemplary embodiment, the interval between the conversion layer 14 and the layer having the function of reflecting light can be made narrower. Therefore, according to the radiation detector 10 of the present exemplary embodiment, as compared to the case where the layer having pressure sensitive adhesiveness is provided between the layer having a function of reflecting light and the conversion layer, the peeling of the layer having the function of reflecting light can be suppressed without degrading the image quality of the radiographic image.

Second Exemplary Embodiment

Next, a second exemplary embodiment will be described. In addition, since the radiation detector 10 of the present exemplary embodiment is different from the first exemplary embodiment in terms of the regions where the pressure sensitive adhesive layer 16 is provided, the region where the pressure sensitive adhesive layer 16 is provided will be described with reference to the drawings.

Figure 9:
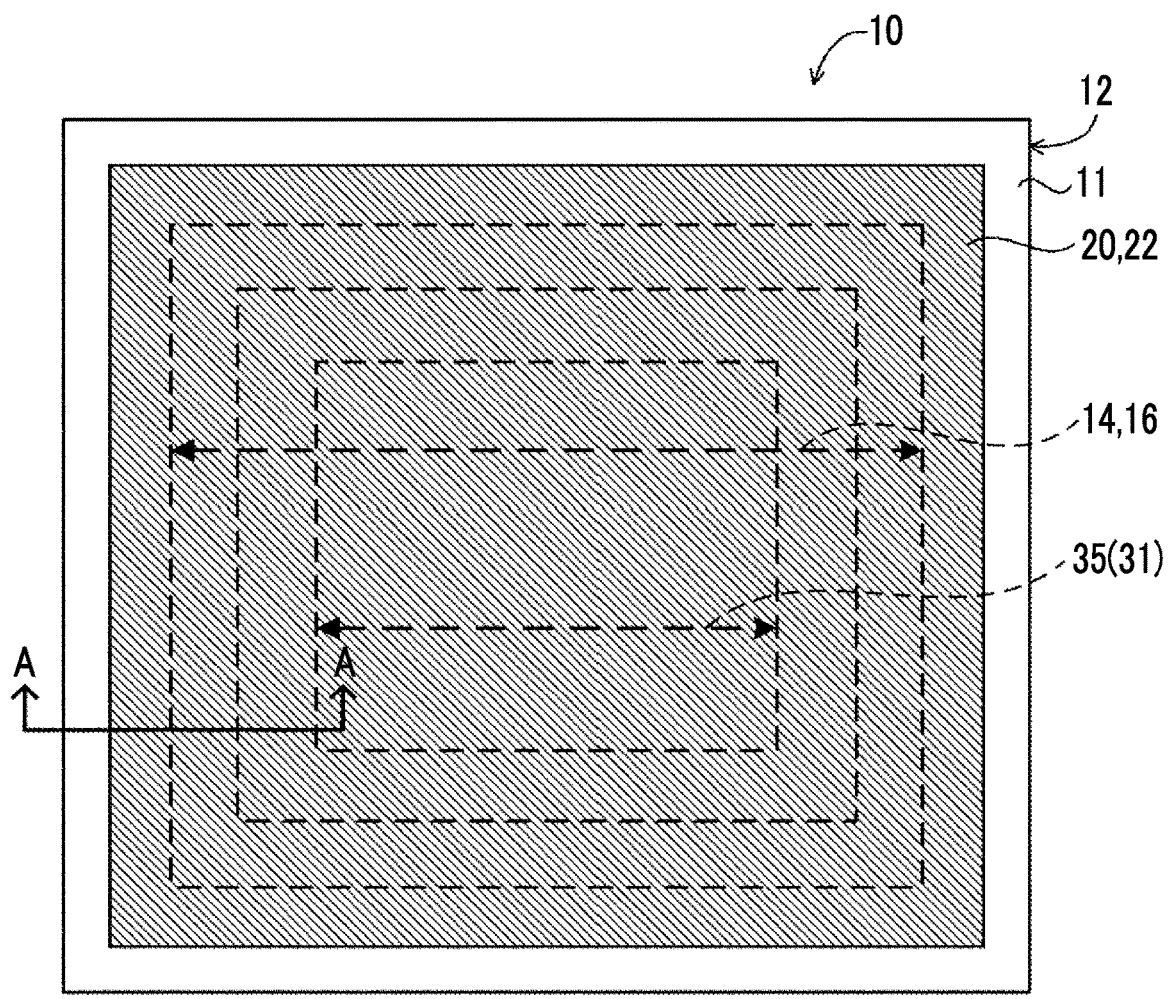
FIG. 9 is a plan view of an example of a radiation detector of a second exemplary embodiment as seen from the side on which a conversion layer is provided.

FIG. 9 is a plan view of the radiation detector 10 of the present exemplary embodiment as seen from the side on which the conversion layer 14 is formed. Additionally, FIG. 10 is a cross-sectional view taken along line A-A of the radiation detector 10 in FIG. 9.

Figure 10:
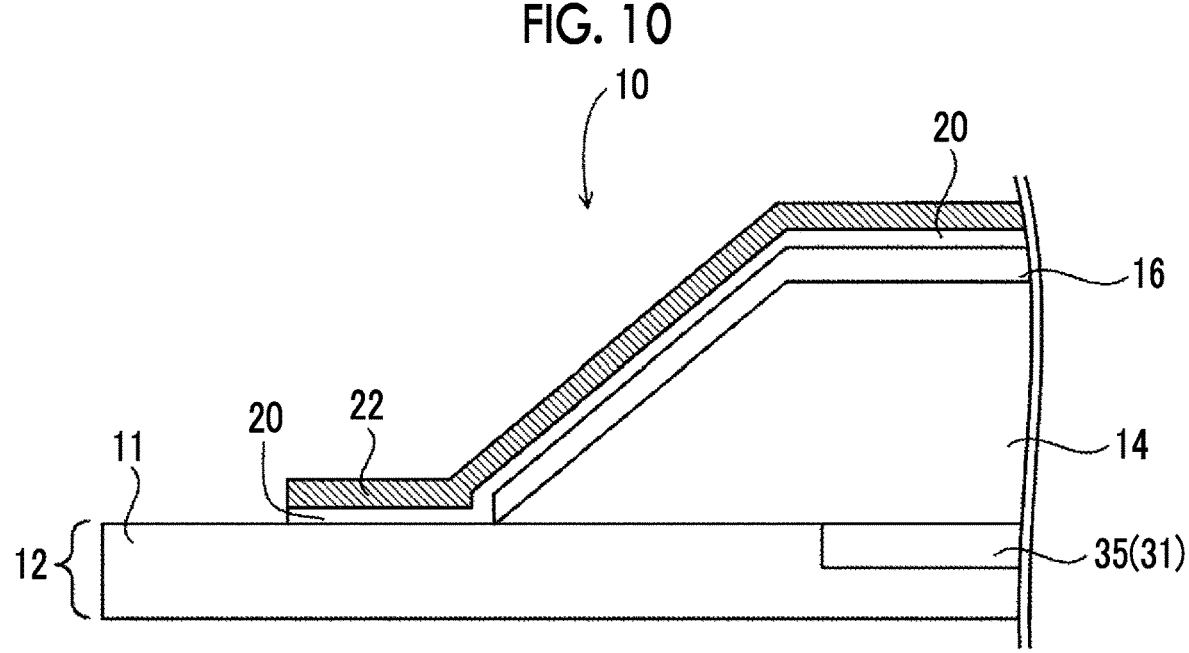
FIG. 10 is a cross-sectional view taken along line A-A of the radiation detector illustrated in FIG. 9.

As illustrated in FIGS. 9 and 10, in the radiation detector 10 of the present exemplary embodiment, the pressure sensitive adhesive layer 16 is provided in the entire region on the conversion layer 14 including the central part and the peripheral edge part. In other words, the pressure sensitive adhesive layer 16 of the present exemplary embodiment covers the entire upper surface of the conversion layer 14.

In addition, the radiation detector 10 of the present exemplary embodiment can be manufactured, for example, by the same manufacturing method as the manufacturing method of the radiation detector 10 that has been described above in the first exemplary embodiment.

In this way, also in the radiation detector 10 of the present exemplary embodiment illustrated in FIGS. 9 and 10, the adhesive layer 20 and the protective layer 22 cover the entire pressure sensitive adhesive layer 16, similarly to the radiation detector 10 of the first exemplary embodiment. Additionally, the adhesive layer 20 and the protective layer 22 are directly fixed onto the TFT substrate 12. Additionally, also in the radiation detector 10 of the present exemplary embodiment, similarly to the radiation detector 10 of the first exemplary embodiment, the reflective pressure sensitive adhesive layer 16 having the function of reflecting light is directly formed on the conversion layer 14. Therefore, according to the radiation detector 10 of the present exemplary embodiment, as compared to the case where the layer having pressure sensitive adhesiveness is provided between the layer having a function of reflecting light and the conversion layer, the peeling of the layer having the function of reflecting light can be suppressed without degrading the image quality of the radiographic image.

Additionally, according to the radiation detector 10 of the present exemplary embodiment, the pressure sensitive adhesive layer 16 is larger compared to the radiation detector 10 of the first exemplary embodiment, and the entire upper surface of the conversion layer 14 is covered. Therefore, the light from the conversion layer 14 is easily reflected.

Third Exemplary Embodiment

Next, a third exemplary embodiment will be described. In addition, since the radiation detector 10 of the present exemplary embodiment is different from the first exemplary embodiment in terms of a region where the adhesive layer 20 is provided, the region where the adhesive layer 20 is provided will be described with reference to the drawings.

Figure 11:
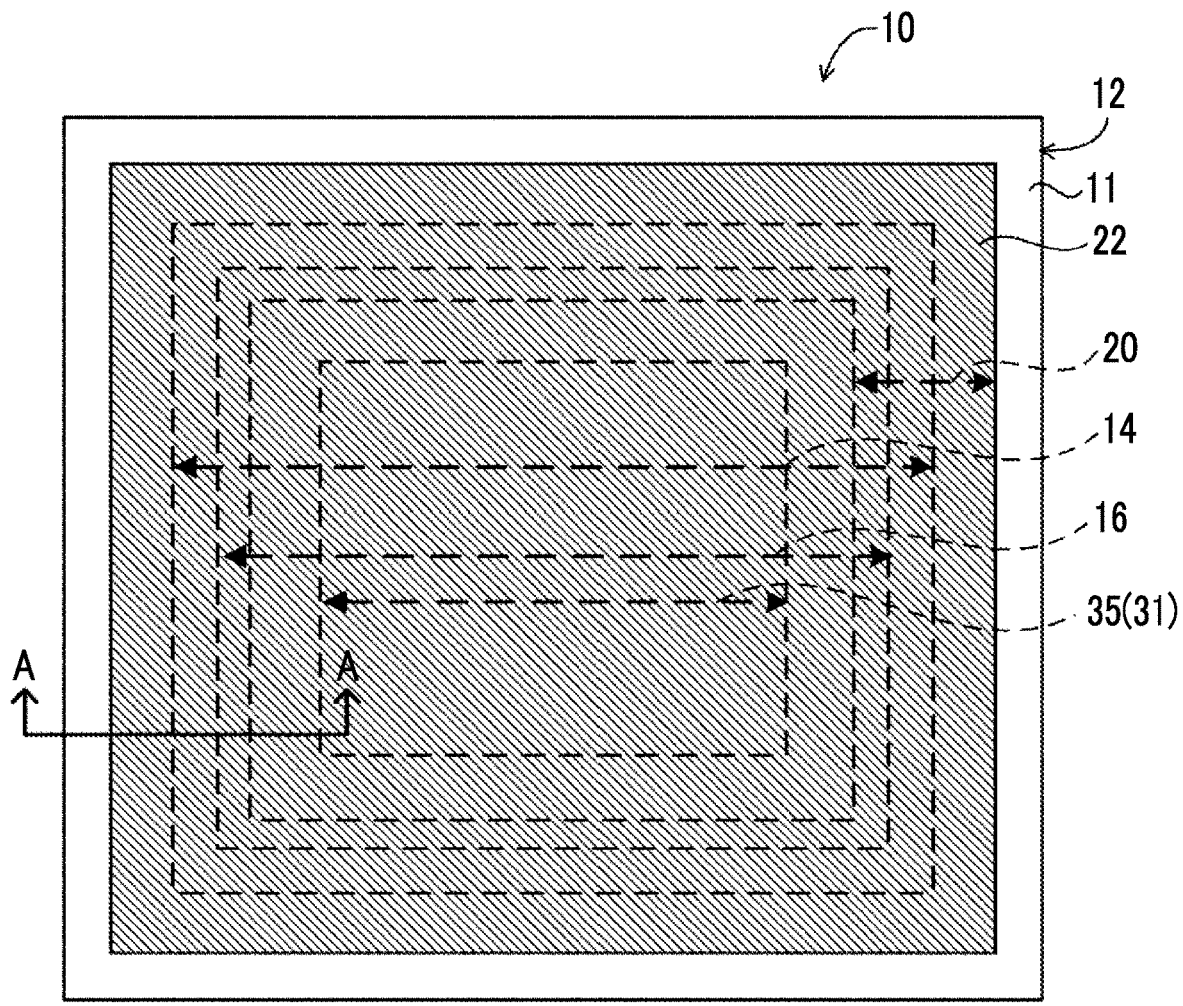
FIG. 11 is a plan view of an example of a radiation detector of a third exemplary embodiment as seen from the side on which a conversion layer is provided.

FIG. 11 is a plan view of the radiation detector 10 of the present exemplary embodiment as seen from the side on which the conversion layer 14 is formed. Additionally, FIG. 12 is a cross-sectional view taken along line A-A of the radiation detector 10 in FIG. 11.

Figure 12:
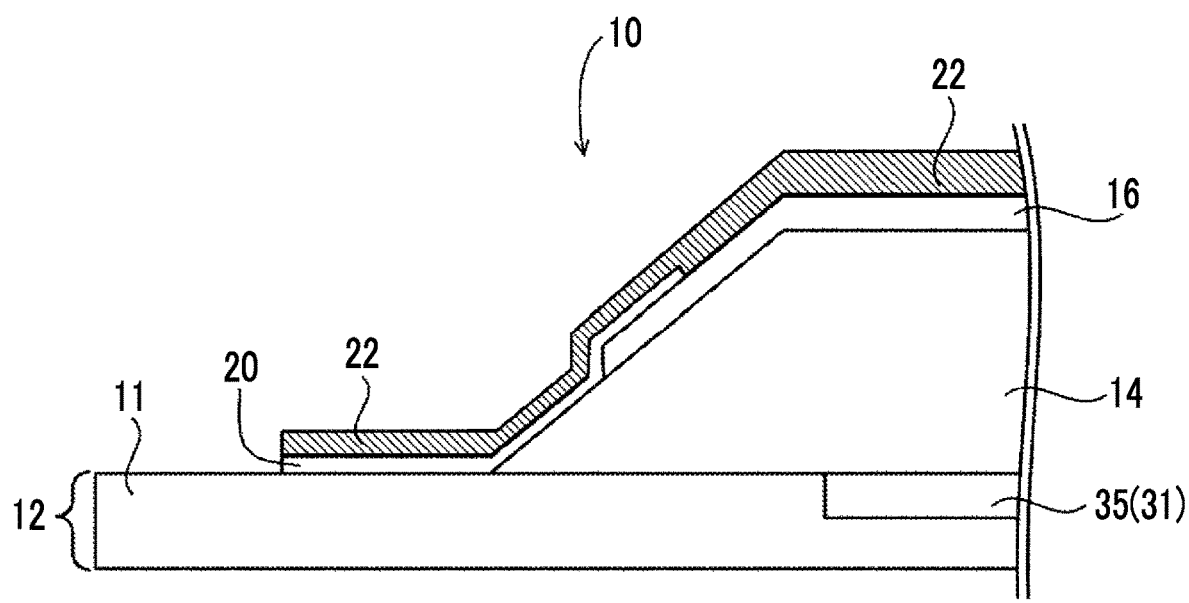
FIG. 12 is a cross-sectional view taken along line A-A of the radiation detector illustrated in FIG. 11.

As illustrated in FIGS. 11 and 12, in the radiation detector 10 of the present exemplary embodiment, the adhesive layer 20 is provided on a region ranging from the TFT substrate 12 in the vicinity of the peripheral edge part of the conversion layer 14 to the outer peripheral part of the pressure sensitive adhesive layer 16. That is, in the radiation detector 10 of the present exemplary embodiment, the adhesive layer 20 does not cover the entire pressure sensitive adhesive layer 16.

In addition, the radiation detector 10 of the present exemplary embodiment can be manufactured, for example, by the same manufacturing method as the manufacturing method of the radiation detector 10 that has been described above in the first exemplary embodiment.

In this way, according to the radiation detector 10 of the present exemplary embodiment illustrated in FIGS. 11 and 12, the adhesive layer 20 covers an outer peripheral part that is an end part of the pressure sensitive adhesive layer 16. Additionally, the adhesive layer 20 and the protective layer 22 are directly fixed onto the TFT substrate 12. Therefore, according to the radiation detector 10 of the present exemplary embodiment, the peeling of the pressure sensitive adhesive layer 16, particularly the peeling of the end part is suppressed by the adhesive layer 20.

Additionally, also in the radiation detector 10 of the present exemplary embodiment, similarly to the radiation detector 10 of the first exemplary embodiment, the reflective pressure sensitive adhesive layer 16 having the function of reflecting light is directly formed on the conversion layer 14. Therefore, also in the radiation detector 10 of the present exemplary embodiment, as compared to the case where the layer having pressure sensitive adhesiveness is provided between the layer having the function of reflecting light and the conversion layer, the peeling of the layer having the function of reflecting light can be suppressed without degrading the image quality of the radiographic image.

Additionally, according to the radiation detector 10 of the present exemplary embodiment, the adhesive layer 20 does not cover the entire upper surface of the conversion layer 14. Therefore, it is possible to suppress that radiation is attenuated by being transmitted through the adhesive layer 20 until the radiation is radiated from the protective layer 22 side and reaches the conversion layer 14.

As described above, the radiation detectors 10 of the first to third exemplary embodiment have a portion in which the TFT substrate 12 in which the plurality of pixels 30 for accumulating the electric charges generated in accordance with the light converted from radiation are formed in the pixel region 35, the conversion layer 14 that converts the radiation into light, the reflective pressure sensitive adhesive layer 16 that reflects the light converted by the conversion layer 14, and the adhesive layer 20 that covers a region including the region ranging from the end part of the pressure sensitive adhesive layer 16 to the surface of the TFT substrate 12 are provided in this order.

For that reason, as described above, according to the radiation detectors 10 of the first to third exemplary embodiments, as compared to the case where the layer having pressure sensitive adhesiveness is provided between the layer having a function of reflecting light and the conversion layer, the peeling of the layer having a function of reflecting light can be suppressed without degrading the image quality of the radiographic image.

Additionally, in a case where the pressure sensitive adhesive layer 16 is peeled, moisture, such as humidity, easily enters the inside of the radiation detector 10 from the peeled portion. The conversion layer 14, particularly the conversion layer 14 using CsI is weak to moisture. Therefore, in a case where the moisture enters the inside of the radiation detector 10, there is a concern that the image quality of a radiographic image to be obtained by the radiation detector 10 may degrade. In contrast, according to the radiation detector 10 of the first to third exemplary embodiments, by suppressing the peeling of the pressure sensitive adhesive layer 16, the entry of the moisture can be suppressed. Therefore, the degradation of the image quality of a radiographic image to be obtained by the radiation detector 10 can be suppressed.

Additionally, in a case where the side surface of the pressure sensitive adhesive layer 16 is exposed, there is a concern that moisture, such as humidity, enters the inside of the radiation detector from the exposed spot. However, in the first to third exemplary embodiments, the side surface of the pressure sensitive adhesive layer 16 is covered with the adhesive layer 20 and the protective layer 22. Therefore, a moisture preventing effect can be enhanced.

Fourth Exemplary Embodiment

Next, a fourth exemplary embodiment will be described. In addition, since the radiation detector 10 of the present exemplary embodiment is different from the above first to third exemplary embodiments in terms of the configuration of the pressure sensitive adhesive layer 16 and the regions where the pressure sensitive adhesive layer 16 are provided, the pressure sensitive adhesive layer 16 and the regions where the pressure sensitive adhesive layer 16 are provided will be described with reference to the drawings.

Figure 13:
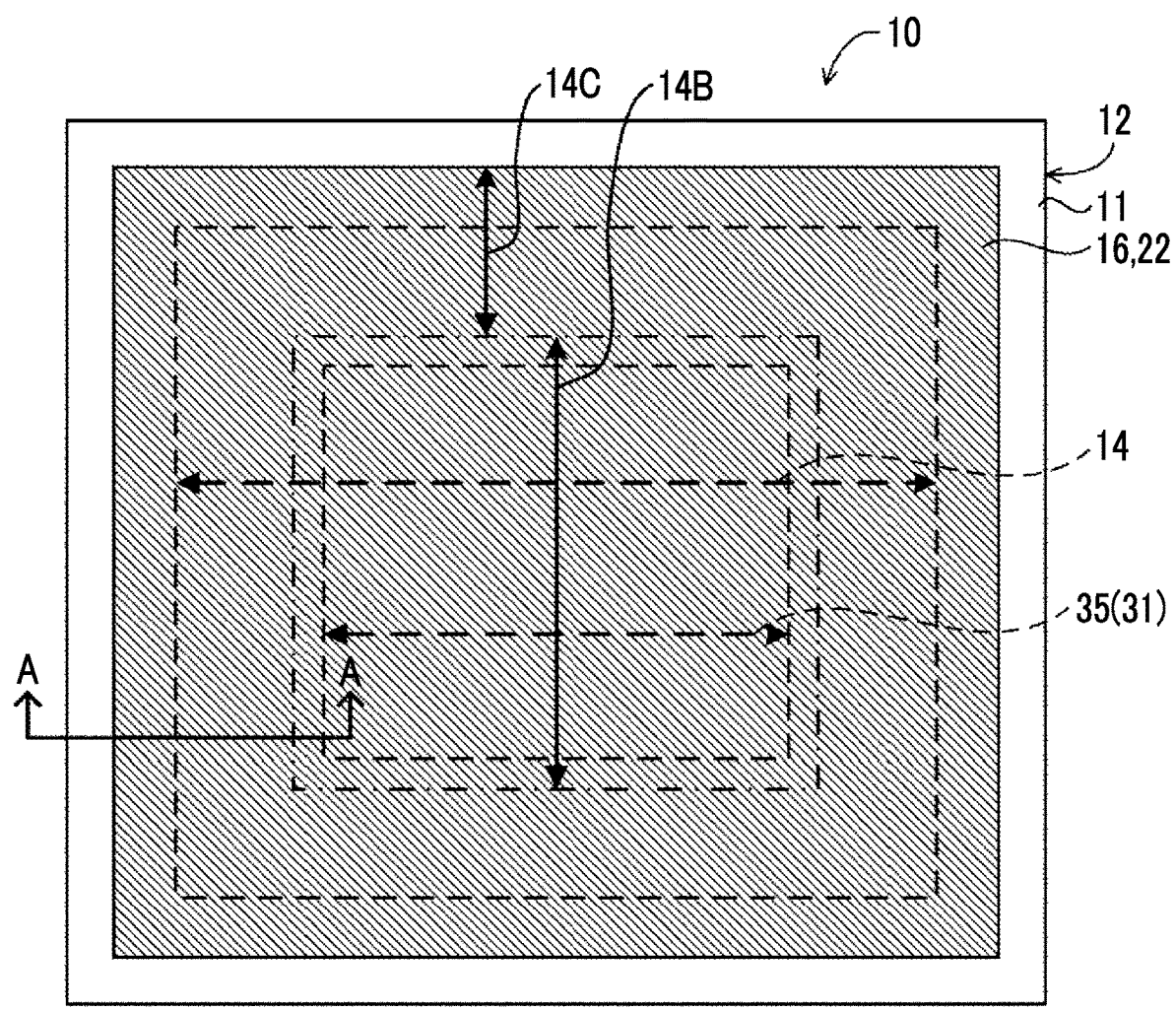
FIG. 13 is a plan view of an example of a radiation detector of a fourth exemplary embodiment as seen from the side on which a conversion layer is provided.
Figure 14:
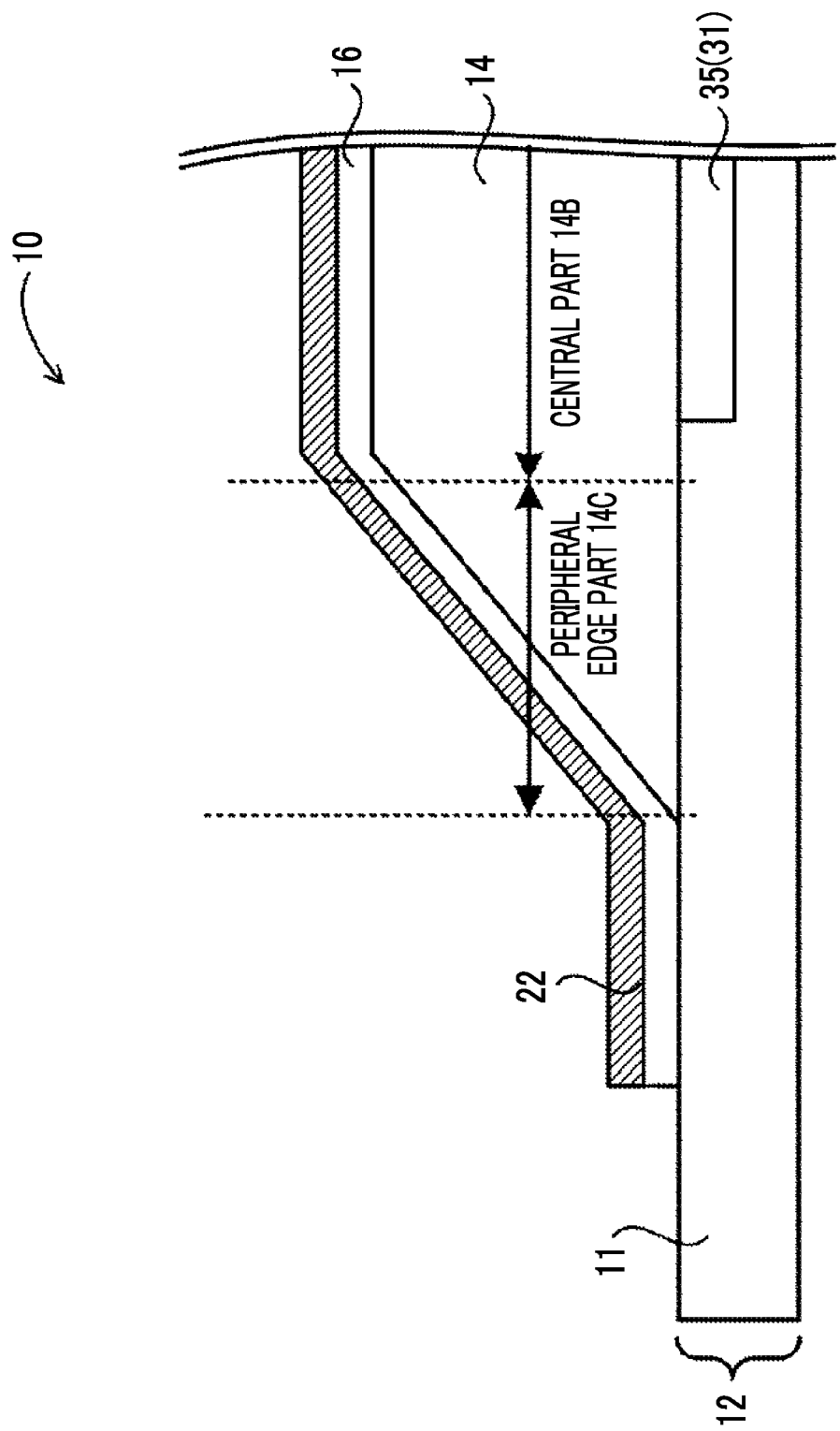
FIG. 14 is a cross-sectional view taken along line A-A of the radiation detector illustrated in FIG. 13.

FIG. 13 is a plan view of the radiation detector 10 of the present exemplary embodiment as seen from the side on which the conversion layer 14 is formed. Additionally, FIG. 14 is a cross-sectional view taken along line A-A of the radiation detector 10 in FIG. 13. Additionally, FIG. 15 illustrates a cross-sectional view schematically illustrating the cross-section of an example of the pressure sensitive adhesive layer 16 and the protective layer 22 of the present exemplary embodiment.

As illustrated in FIGS. 13 and 14, in the radiation detector 10 of the present exemplary embodiment, the pressure sensitive adhesive layer 16 is provided in the entire region on the conversion layer 14 including the central part 14B and the peripheral edge part 14C, and a region on the TFT substrate 12 in the vicinity of the outer periphery of the conversion layer 14. Additionally, as illustrated in FIGS. 14 and 15, the radiation detector 10 of the present exemplary embodiment is different from the radiation detector 10 of the first to third exemplary embodiments in that the protective layer 22 is directly provided on the pressure sensitive adhesive layer 16 and the adhesive layer 20 is not provided.

In the present exemplary embodiment, a pressure sensitive adhesive layer made of a thermoplastic resin in which an inorganic white powder is dispersed is used as an example of the pressure sensitive adhesive layer 16. As the thermoplastic resin in this case, a so-called hot-melt resin can be used, and specific examples, a polyolefin-based resin, a polyester-based resin, EVA, and the like can be used. Similarly to the pressure sensitive adhesive layer 16 described above in the first to third exemplary embodiments, examples of the inorganic white powder include a powder containing at least one of titanium oxide ($TiO_2$), barium sulfate ($BaSO_4$), alumina ($Al_2O_3$), magnesium oxide (MgO), calcium oxide (CaO), or the like.

Figure 15:
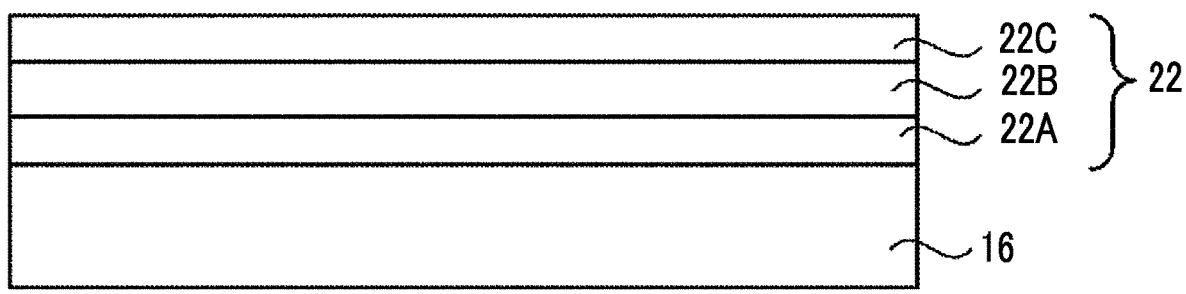
FIG. 15 is a cross-sectional view schematically illustrating a cross-section of an example of a pressure sensitive adhesive layer and a protective layer of a fourth exemplary embodiment.

As illustrated in FIG. 15, as an example, the protective layer 22 in the radiation detector 10 according to the present exemplary embodiment is also a laminated film in which the PET film 22A, the aluminum foil film 22B, and the PET film 22C are laminated.

An example of a method of manufacturing the radiation detector 10 of the present exemplary embodiment includes the following method.

A preparation is made in advance by directly applying the pressure sensitive adhesive layer 16 to the protective layer 22 having a desired size adapted to the radiation detector 10. In addition, in the radiation detector 10 of the present exemplary embodiment, the pressure sensitive adhesive layer 16 also plays a role of sealing the end part of the protective layer 22. Therefore, the pressure sensitive adhesive layer 16 is applied to the entire surface of the protective layer 22. Meanwhile, the conversion layer 14 is formed directly on the TFT substrate 12, by the vapor-phase deposition methods as described above. Then, the pressure sensitive adhesive layer 16 applied to the protective layer 22 is bonded to the TFT substrate 12 to seal the conversion layer 14.

In this way, the radiation detector 10 of the present exemplary embodiment illustrated in FIGS. 13 to 15 has a portion in which the TFT substrate 12 in which the plurality of pixels 30 that accumulate the electric charges generated in accordance with the light converted from the radiation are formed in the pixel region 35, the conversion layer 14 that converts the radiation into light, and the reflective pressure sensitive adhesive layer 16 that reflects the light converted by the conversion layer 14 and covers the entire conversion layer 14 and a region including the region ranging to the surface of the TFT substrate 12 are provided in this order.

Additionally, the radiation detector 10 of the present exemplary embodiment includes a portion in which the TFT substrate 12 in which the plurality of pixels 30 that accumulate the electric charges generated in accordance with the light converted from the radiation are formed in the pixel region 35, the conversion layer 14 that converts the radiation into light, and the protective layer 22 that has a laminated structure in which the protective layer 22 is laminated on the reflective pressure sensitive adhesive layer 16 that covers at least the conversion layer 14 and that covers the entire conversion layer 14 and a region including the region ranging to the surface of the TFT substrate 12 are provided in this order, and the pressure sensitive adhesive layer 16 of the protective layer 22 is disposed on the conversion layer 14 side.

In the radiation detector 10 of the present exemplary embodiment, the pressure sensitive adhesive layer 16 covers the entire conversion layer 14 and further covers the surface of the base material 11. Therefore, the pressure sensitive adhesive layer 16 can be sufficiently fixed to the end parts of the TFT substrate 12 and the conversion layer 14. Additionally, in the radiation detector 10 of the present exemplary embodiment, the pressure sensitive adhesive layer 16 is directly provided on the conversion layer 14. Therefore, also in the radiation detector 10 of the present exemplary embodiment, similarly to the radiation detectors 10 of the first to third exemplary embodiments, as compared to the case where the layer having pressure sensitive adhesiveness is provided between the layer having a function of reflecting light and the conversion layer 14, the peeling of the pressure sensitive adhesive layer 16 can be suppressed without degrading the image quality of the radiographic image.

Figure 16:
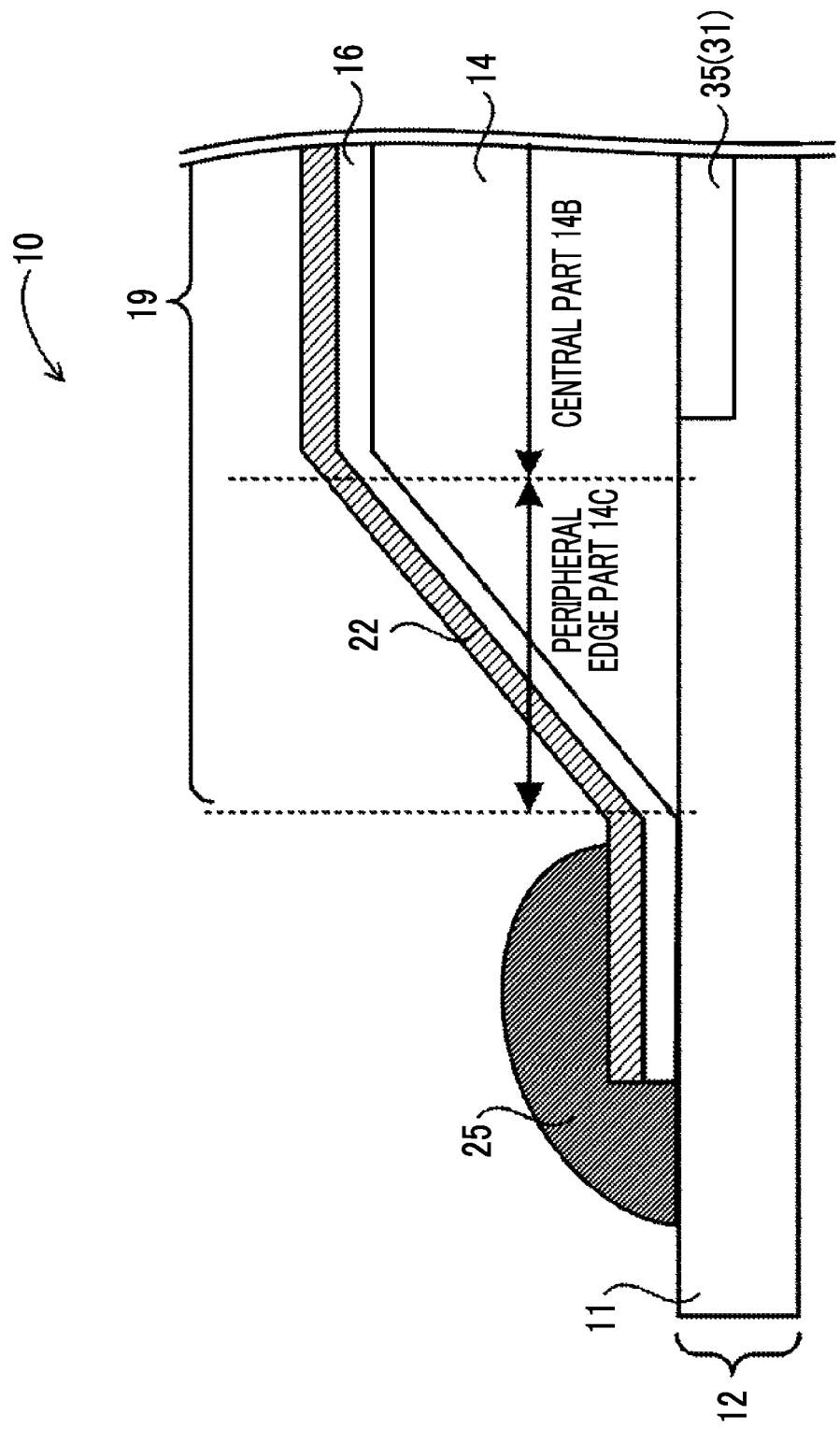
FIG. 16 is a cross-sectional view of another example of the radiation detector of the fourth exemplary embodiment.

In addition, the radiation detector 10 of the present exemplary embodiment may have a form in which the outer peripheries of the protective layer 22 and the pressure sensitive adhesive layer 16 are sealed with a sealant 25, as in the example illustrated in FIG. 16. The sealant 25 preferably covers the side surfaces of the protective layer 22 and the pressure sensitive adhesive layer 16, and is preferably provided in a region ranging from the surface of the TFT substrate 12 to the surface of the protective layer 22 and does not cover the pixel region 35. As the sealant, a sealant in which a resin is used for a material is preferable, and a sealant in which a thermoplastic resin is used is more preferable. Examples of the sealant include acrylic glue, urethane glue, and the like.

By providing the sealant 25 as in the example illustrated in FIG. 16, the peeling of the end part of the pressure sensitive adhesive layer 16 can be further suppressed.

Fifth Exemplary Embodiment

Figure 17:
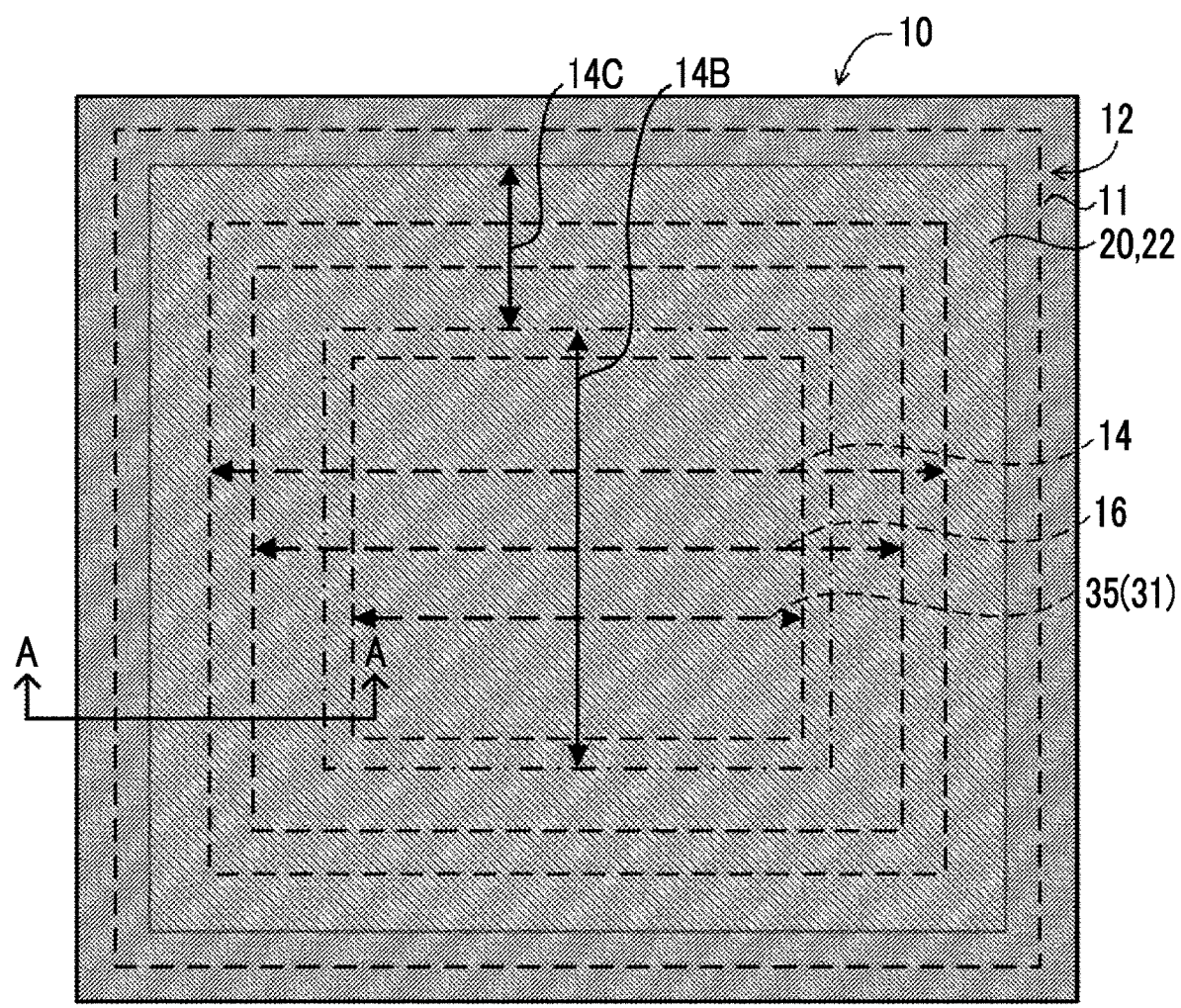
FIG. 17 is a plan view of an example of a radiation detector of a fifth exemplary embodiment as seen from the side on which a conversion layer is provided.

In the present exemplary embodiment, a radiation detector 10 including a reinforcing substrate that reinforces the base material 11 will be described. FIG. 17 is a plan view of the radiation detector 10 of the present exemplary embodiment as seen from the side on which the conversion layer 14 is formed. Additionally, FIG. 18 is a cross-sectional view taken along line A-A of the radiation detector 10 in FIG. 17.

Figure 18:
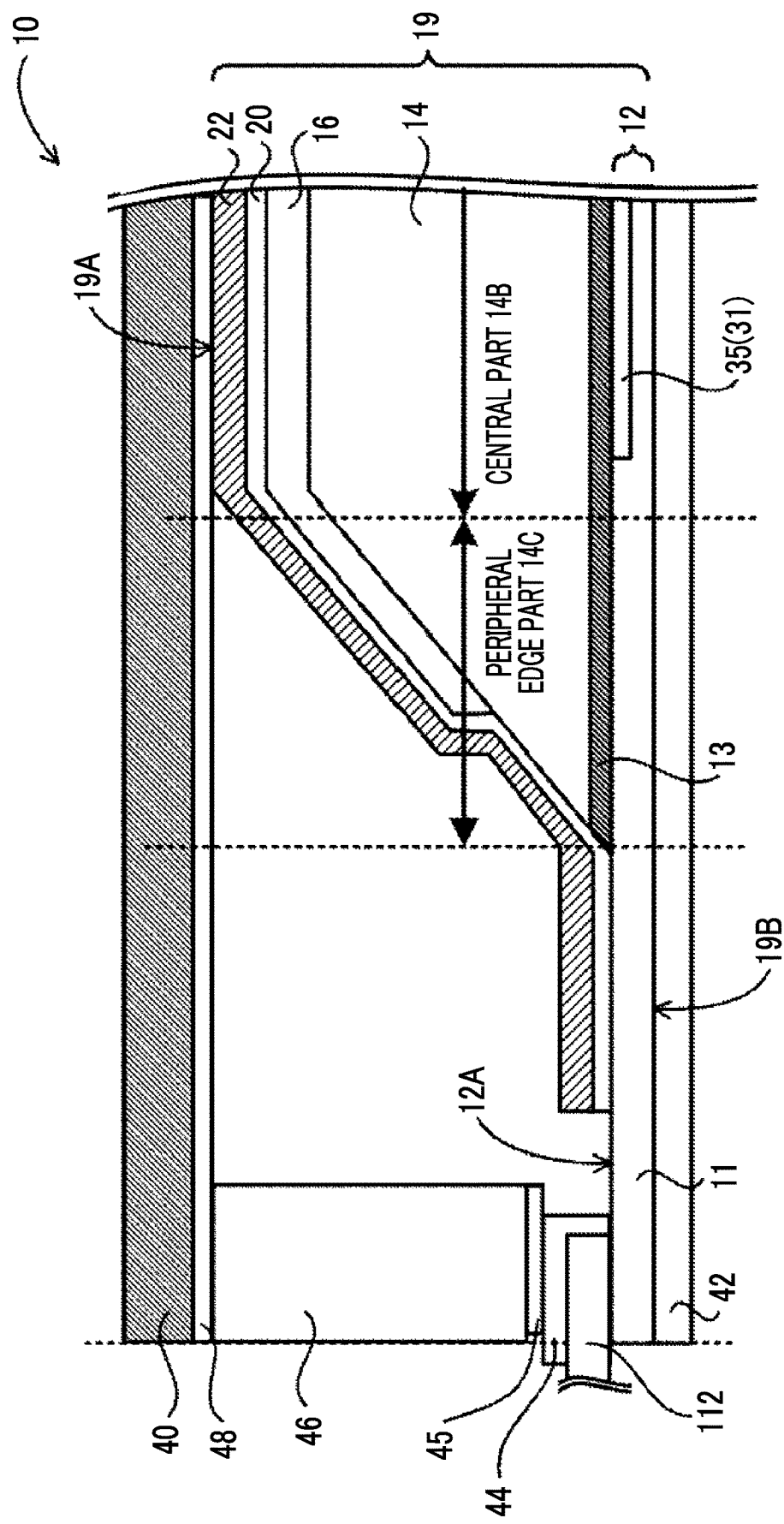
FIG. 18 is a cross-sectional view taken along line A-A of the radiation detector illustrated in FIG. 17.

As illustrated in FIGS. 17 and 18, a reinforcing substrate 40 is provided by a pressure sensitive adhesive layer 48 on a first surface 19A, which is the surface, on the conversion layer 14 side, of a laminate 19 in which the TFT substrate 12, a buffer layer 13, the conversion layer 14, and the protective layer 22 are laminated.

The reinforcing substrate 40 has higher stiffness than the base material 11, and a change in dimension (deformation) due to a force applied in a direction perpendicular to the surface facing the first surface 19A is smaller than a dimensional change due to a force applied perpendicular to the first surface 19A of the base material 11. Additionally, the thickness of the reinforcing substrate 40 of the present exemplary embodiment is larger than the thickness of the base material 11.

The reinforcing substrate 40 is a substrate having plastic as a material. The plastic used as the material of the reinforcing substrate 40 is preferably a thermoplastic resin and includes at least one of polycarbonate (PC), polyethylene terephthalate (PET), styrene, acrylic, polyacetase, nylon, polypropylene, ABS, engineering plastics, or polyphenylene ether. In addition, the reinforcing substrate 40 is preferably at least one of polypropylene, ABS, engineering plastics, polyethylene terephthalate, or polyphenylene ether among them, more preferably at least one of styrene, acrylic, polyacetase, or nylon, and more preferably at least one of polycarbonate or polyethylene terephthalate.

As illustrated in FIG. 18, the reinforcing substrate 40 of the present exemplary embodiment is provided in a region wider than the region of the first surface 12A of the TFT substrate 12 in which the conversion layer 14 is provided. For that reason, as illustrated in FIGS. 3 and 4, the end part of the reinforcing substrate 40 protrudes outward from an outer peripheral part of the conversion layer 14 (the outer peripheral part side of the TFT substrate 12).

A flexible cable 112, the details of which will be described below, is connected to the outer peripheral part of the TFT substrate 12. A spacer 46 that seals the side surfaces of the conversion layer 14 is provided with the flexible cable 112, a moisture proof agent 44, and a pressure sensitive adhesive layer 45 interposed between the reinforcing substrate 40 and the first surface 12A of the TFT substrate 12. The spacer 46 of the present exemplary embodiment is an example of a sealing member of the present disclosure.

The method of providing the spacer 46 is not particularly limited, and for example, the spacer 46 may be provided between the TFT substrate 12 and the reinforcing substrate 40 by bonding the spacer 46 to the pressure sensitive adhesive layer 48 of the end part of the reinforcing substrate 40 and bonding the reinforcing substrate 40 in a state where the spacer 46 is provided, to the TFT substrate 12 in a state where the laminate 19, the flexible cable 112, the moisture proof agent 44, and the pressure sensitive adhesive layer 45 are provided. In addition, the width of the spacer 46 (in the direction intersecting a lamination direction of the laminate 19) is not limited to the example illustrated in FIG. 18. For example, the width of the spacer 46 may be expanded to a position closer to the conversion layer 14 than the example illustrated in FIG. 18.

Additionally, a protective film 42 having a function of protecting from moisture such as humidity is provided on a second surface 19B that is the surface, on the TFT substrate 12 side, of the laminate 19 of the present exemplary embodiment. Examples of the material of the protective film 42 include the same materials as the protective layer 22.

An example of a method of manufacturing the radiation detector 10 of the present exemplary embodiment includes the following method.

In advance, the pressure sensitive adhesive layer 48 is applied to the reinforcing substrate 40 having a desired size adapted to the radiation detector 10, and the spacer 46 is provided on the pressure sensitive adhesive layer 48. Meanwhile, similarly to the first exemplary embodiment (refer to FIG. 7), the TFT substrate 12 is formed on the support body 50 such as a glass substrate having a larger thickness than the base material 11 via the peeling layer 52, for example, by the lamination method or the like. Moreover, the conversion layer 14 is directly formed on the TFT substrate 12 by the vapor-phase deposition method as described above, and the flexible cable 112, the moisture proof agent 44, and the pressure sensitive adhesive layer 45 are provided. Then, the reinforcing substrate 40 provided with the spacers 46 is bonded to the TFT substrate 12 having the conversion layer 14 formed thereon, thereby sealing the conversion layer 14.

Here, in a case where the TFT substrate 12 is peeled from the support body 50, the TFT substrate 12 is easily bent because the base material 11 has flexibility. In a case where the TFT substrate 12 is largely bent, the TFT substrate 12 is also largely bent. As a result, there is a concern that the conversion layer 14 may be damaged. Additionally, the present invention is not limited to a case where the TFT substrate 12 is peeled from the support body 50. In a case where the radiation detector 10 is handled as a single body during the manufacturing process of the radiographic imaging apparatus 1, there is a concern that the conversion layer 14 may be damaged the bending of the TFT substrate 12. In contrast, in the radiation detector 10 of the present exemplary embodiment, the reinforcing substrate 40 is provided on the first surface 19A that is the surface of the laminate 19 on the conversion layer 14 side. Therefore, large bending of the TFT substrate 12 can be suppressed, and damage of the conversion layer 14 can be suppressed.

Figure 19:
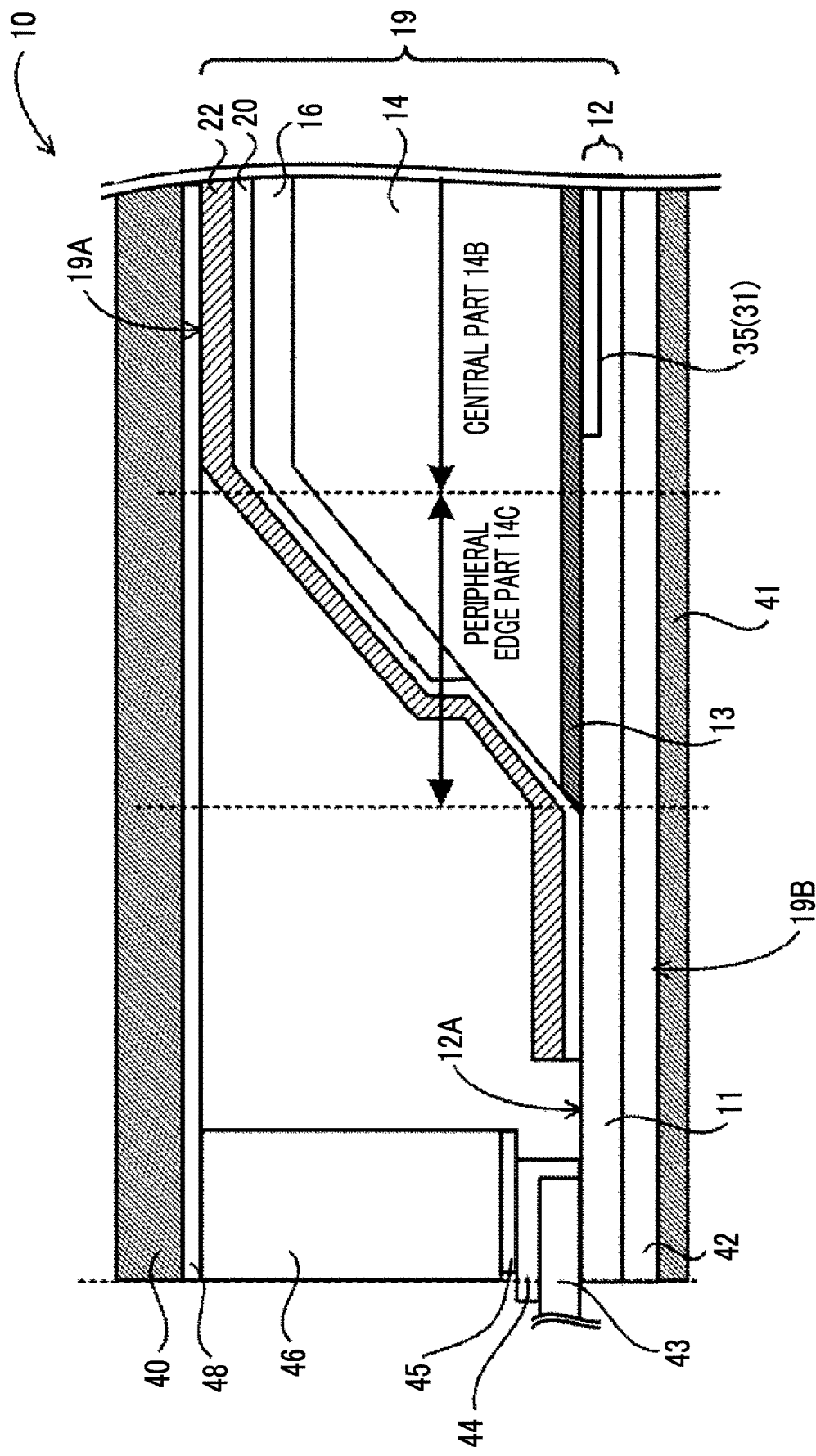
FIG. 19 is a cross-sectional view taken along line A-A of another example of the radiation detector of the fifth exemplary embodiment.
Figure 20:
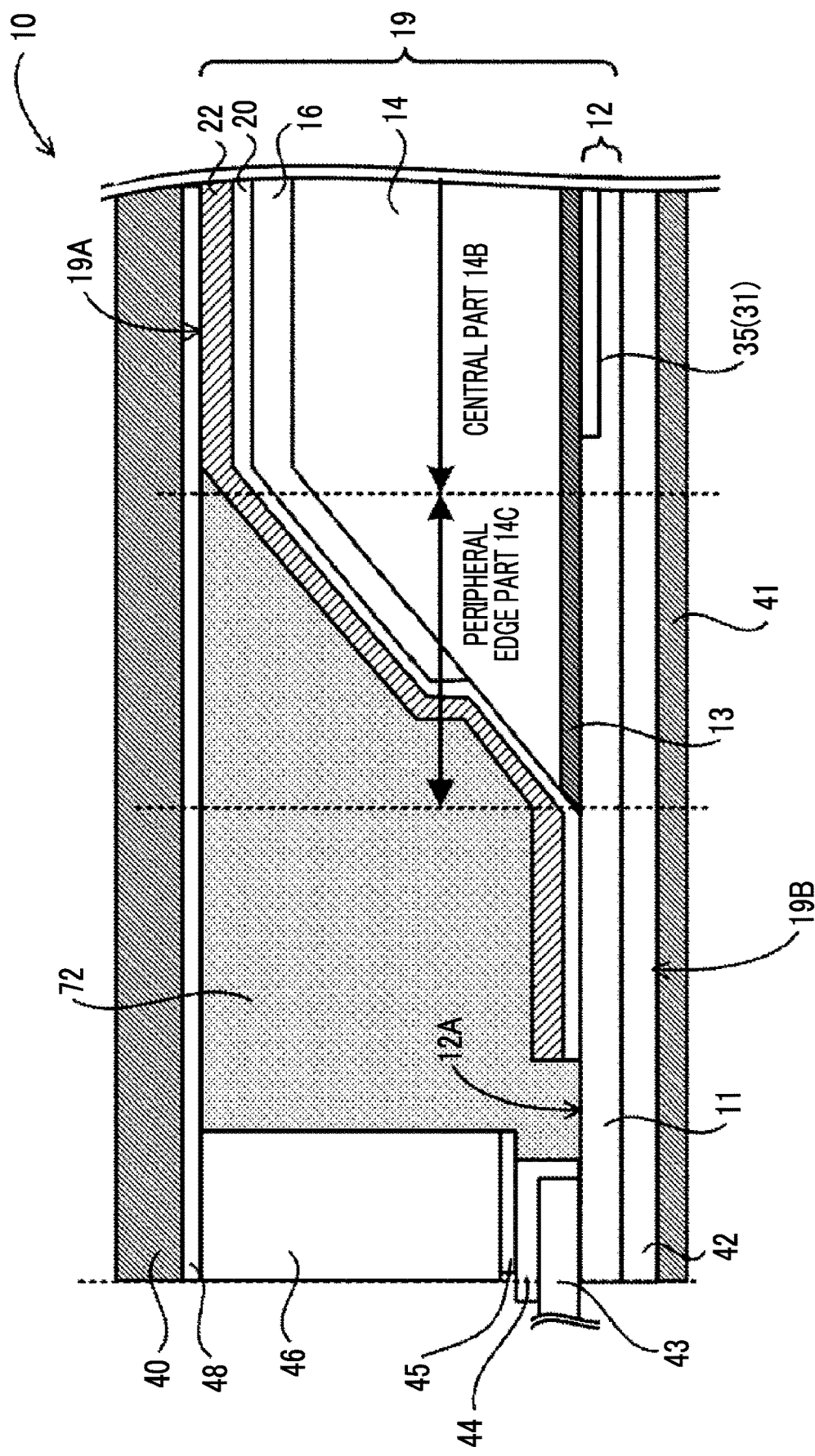
FIG. 20 is a cross-sectional view taken along line A-A of another example of the radiation detector of the fifth exemplary embodiment.

In addition, the reinforcing substrate 40 is not limited to the form illustrated in FIGS. 17 and 18, and the reinforcing substrate may be provided on at least one of the first surface 19A or the second surface 19B of the laminate 19. For example, as in the example illustrated in FIG. 19, a form may be adopted in which the reinforcing substrate 40 is provided on the first surface 19A of the laminate 19 and the reinforcing substrate 41 is provided on the second surface 19B. In this case, the thickness of the reinforcing substrate 41 is smaller than the thickness of the reinforcing substrate 40. Additionally, as in the example illustrated in FIG. 20, a form may be adopted in which at least a portion of the space between the first surface 12A of the TFT substrate 12 and the reinforcing substrate 40 may be filled with a filling material 72.

In this way, the radiation detector 10 of the present exemplary embodiment includes at least one of the reinforcing substrate 40 or the reinforcing substrate 41. Accordingly, even in the radiation detector 10 alone, the TFT substrate 12 can be inhibited from being largely bent, and the conversion layer 14 can be inhibited from being damaged.

Figure 21:
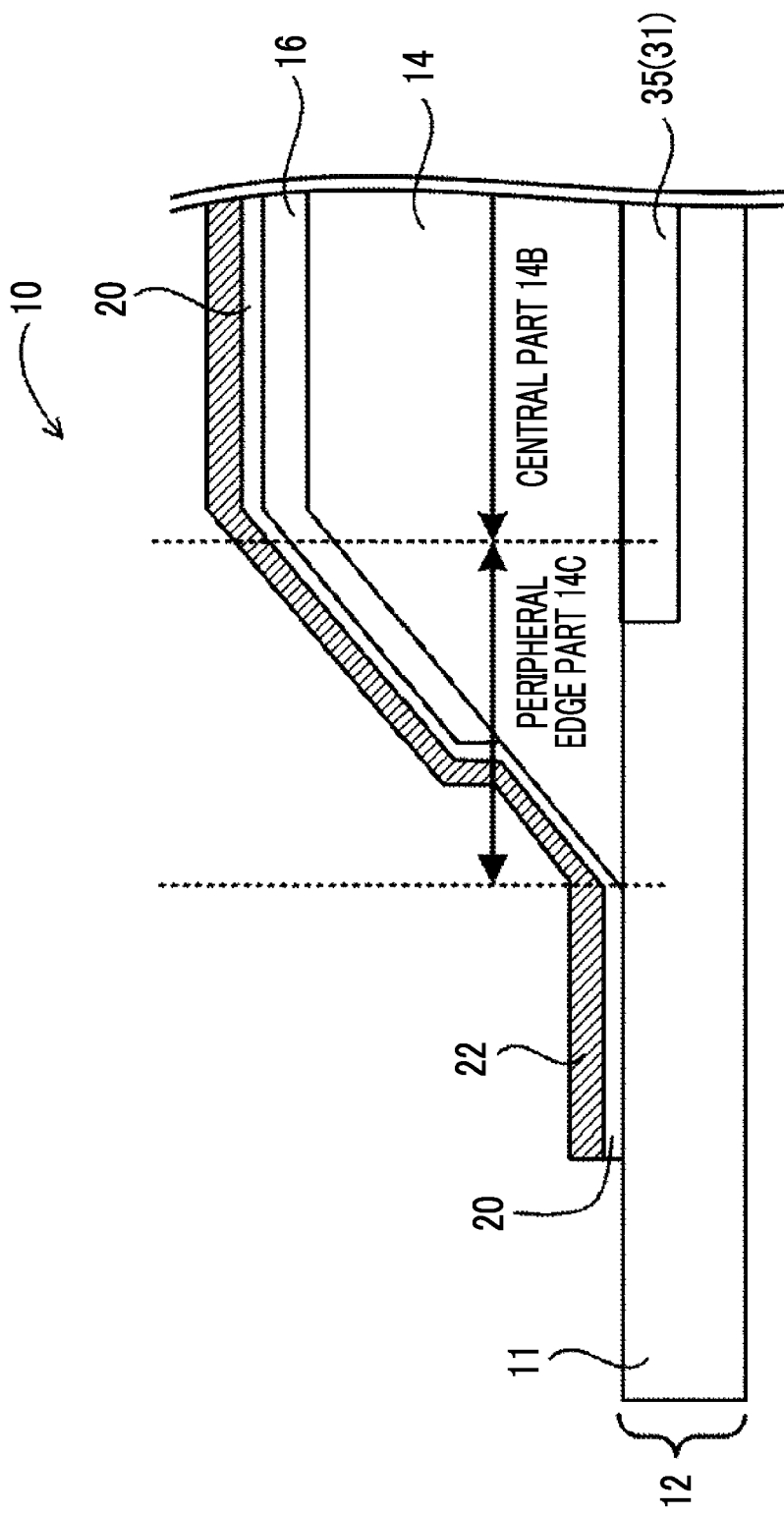
FIG. 21 is a cross-sectional view illustrating the cross-section of an example of a radiation detector in which the size of a pixel region is small, as a modification example of the size of the pixel region.

In addition, the radiation detector 10 according to the technique of the present disclosure is not limited to the above respective exemplary embodiments. In addition, the size of the pixel array 31 (pixel region 35) is not limited to that of the above respective exemplary embodiments. For example, in the above respective exemplary embodiments, a form has been described in which the size of the pixel array 31 (pixel region 35) is smaller than the size of the central part 14B of the conversion layer 14, and the outer periphery of the pixel array 31 (pixel region 35) is within the central part 14B. However, the size of the pixel array 31 (pixel region 35) is not limited to the above form. As in the radiation detector 10 of the example illustrated in FIG. 21, a form may be adopted in which the size of the pixel array 31 (pixel region 35) is larger than the size of the central part 14B of the conversion layer 14, and the outer periphery of the pixel array 31 (pixel region 35) reaches the peripheral edge part 14C of the conversion layer 14. In addition, the amount of light converted from the radiation in the conversion layer 14 tends to decrease as the thickness of the conversion layer 14 becomes smaller. Therefore, similarly to the radiation detector 10 in each of the above respective exemplary embodiments, in a form in which the outer periphery of the pixel array 31 (pixel region 35) is in the central part 14B, the thickness of the conversion layer 14 on the pixel array 31 (pixel region 35) becomes substantially uniform. Therefore, the sensitivity characteristic of the pixel region 35 is improved.

Additionally, in the above respective exemplary embodiments, as illustrated in FIG. 1, an aspect in which the pixels 30 are two-dimensionally arranged in a matrix has been described. However, the invention is not limited to the aspect, and for example, the pixels 30 may be one-dimensionally arranged or may be arranged in a honeycomb shape. Additionally, the shape of the pixels is also not limited, and may be a rectangular shape, or may be a polygonal shape, such as a hexagonal shape. Moreover, it goes without saying that the shape of the pixel array 31 (pixel region 35) is also not limited.

Additionally, the shape or the like of the conversion layer 14 is also not limited to the above respective exemplary embodiments. In the above respective exemplary embodiments, an aspect in which the shape of the conversion layer 14 is a rectangular shape similar to the shape of the pixel array 31 (pixel region 35) has been described. However, the shape of the conversion layer 14 may not be the same shape as the pixel array 31 (pixel region 35). Additionally, the shape of the pixel array 31 (pixel region 35) may not be a rectangular shape but may be, for example, other polygonal shapes or a circular shape.

In addition, in the above respective exemplary embodiments, as an example, a form in which the conversion layer 14 of the radiation detector 10 is the scintillator including CsI has been described. However, the conversion layer 14 may be a scintillator in which GOS or the like is dispersed in a binder, such as resin. The conversion layer 14 using GOS is formed, for example, by directly applying the binder having the GOS dispersed therein onto the TFT substrate 12, the peeling layer, and the like and then drying and solidifying the binder. As a method of forming the conversion layer 14, for example, a Giza method of applying an application liquid to a region where the conversion layer 14 is formed while controlling the thickness of an applied film may be adopted. In addition, in this case, surface treatment for activating the surface of the pixel array 31 may be performed before the binder having the GOS dispersed therein is applied. Additionally, an interlayer insulation film may be provided as a surface protective film on the surface of the pixel array 31.

In a case where the conversion layer 14 using GOS is directly applied onto the surface of the pixel array 31, the end part sags, and similarly to the above-described conversion layer 14 using the CsI, the inclined part is formed at the end part of the conversion layer 14, and the pressure sensitive adhesive layer 16 is easily peeled. In contrast, as described above, the entirety or the outer peripheral part of the pressure sensitive adhesive layer 16 is covered with the adhesive layer 20 having an adhesive force stronger than the adhesive force of the pressure sensitive adhesive layer 16. Accordingly, the pressure sensitive adhesive layer 16 can be more firmly fixed. Therefore, also in the radiation detector 10 having the conversion layer 14 using GOS, the peeling of the end part of the pressure sensitive adhesive layer 16 can be suppressed.

In addition, the radiation detectors 10 of the above respective exemplary embodiments may be applied to an irradiation side sampling (ISS) type radiographic imaging apparatus in which radiation is radiated from the TFT substrate 12 side or may be applied to a penetration side sampling (PSS) type radiographic imaging apparatus in which radiation is radiated from the conversion layer 14 side.

Figure 22:
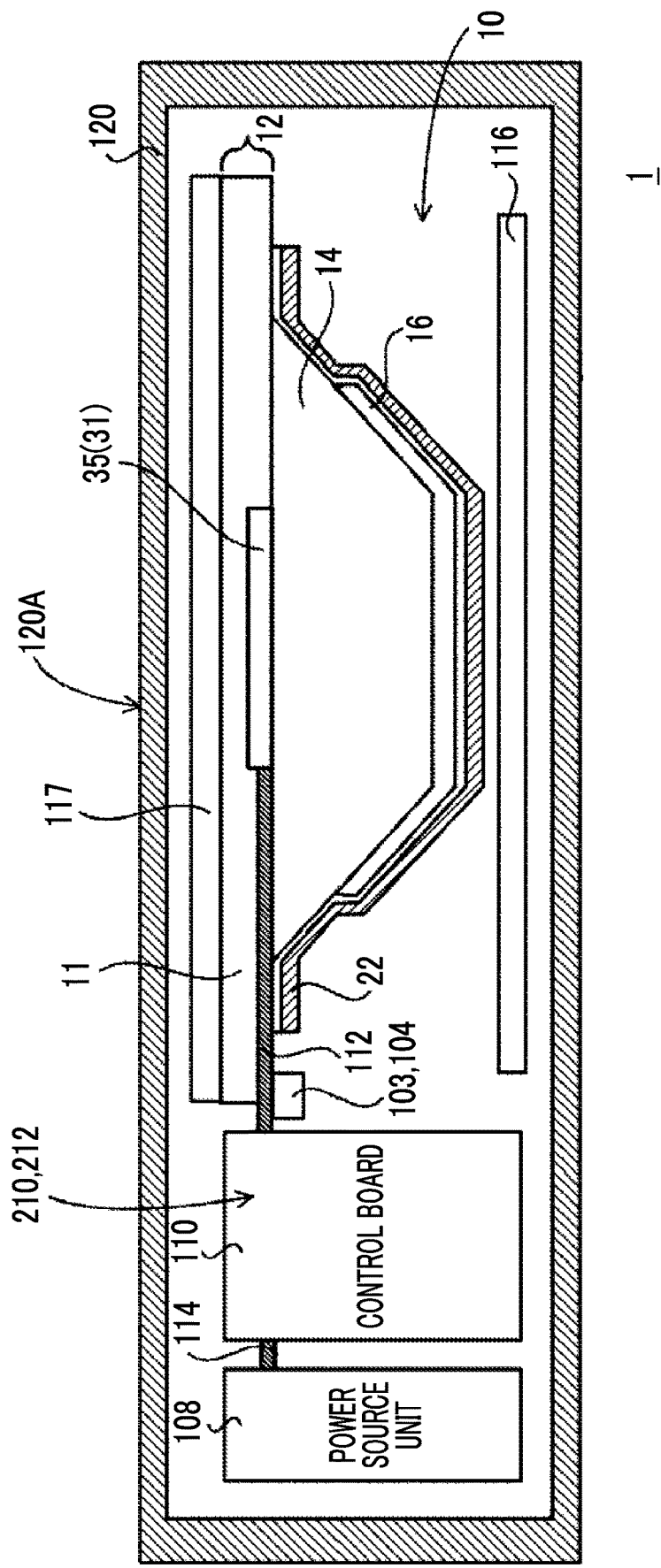
FIG. 22 is a cross-sectional view illustrating the cross-section of an example of a radiographic imaging apparatus to which the radiation detector of the exemplary embodiment is applied.

A cross-sectional view of an example in a state where the radiation detector 10 of the first exemplary embodiment is applied to an irradiation side sampling type radiographic imaging apparatus 1 is illustrated in FIG. 22.

As illustrated in FIG. 22, the radiation detector 10, the power source unit 108, and a control board 110 are provided side by side in a direction intersecting an incidence direction of radiation within the housing 120. The radiation detector 10 is provided in a state where a side where the conversion layer 14 of the pixel array 31 is not provided faces an imaging surface 120A side of the housing 120 that is irradiated with radiation transmitted through the subject.

The control board 110 is a board in which an image memory 210 for storing image data according to the electric charges read from the pixels 30 of the pixel array 31, a control unit 212 for controlling reading or the like of the electric charges from the pixels 30, and the like are formed, and is electrically connected to the pixels 30 of the pixel array 31 by a flexible cable 112 including a plurality of signal wiring lines. In addition, in the radiographic imaging apparatus 1 illustrated in FIG. 22, the control board 110 is a so-called chip on film (COF) in which a drive unit 103 for controlling the switching states of the TFTs 32 of the pixels 30 under the control of the control unit 212, and a signal processing unit 104 for creating and outputting image data according to the electric charges read from the pixels 30 are provided on the flexible cable 112. However, at least one of the drive unit 103 or the signal processing unit 104 may be formed in the control board 110.

Additionally, the control board 110 is connected to the power source unit 108, which supplies electrical power to the image memory 210, the control unit 212, and the like that are formed in the control board 110, by a power source line 114.

A sheet 116 is further provided on a side from which the radiation transmitted through the radiation detector 10 is emitted, within the housing 120 of the radiographic imaging apparatus 1 illustrated in FIG. 22. The sheet 116 is, for example, a copper sheet. The copper sheet does not easily generate secondary radiation due to incident radiation, and therefore, has a function of preventing scattering to the rear side, that is, the conversion layer 14 side. In addition, it is preferable that the sheet 116 covers at least an entire surface of the conversion layer 14 from which radiation is emitted, and covers the entire conversion layer 14.

Additionally, a protective layer 117 is further provided on a side (imaging surface 120A side) to which radiation is incident, within the housing 120 of the radiographic imaging apparatus 1 illustrated in FIG. 22. As the protective layer 117, moisture proof films, such as an ALPET (registered trademark) sheet obtained by laminating aluminum, for example by causing aluminum foil to adhere to the insulating sheet (film), a parylene (registered trademark) film, and an insulating sheet (film), such as polyethylene terephthalate, can be applied. The protective layer 117 has a moisture proof function and an antistatic function with respect to the pixel array 31. For that reason, it is preferable that the protective layer 117 covers at least the entire surface of the pixel array 31 on the side to which radiation is incident, and it is preferable to cover the entire surface of the TFT substrate 12 on the side to which radiation is incident.

In addition, although FIG. 22 illustrates a form in which both the power source unit 108 and the control board 110 are provided on one side of the radiation detector 10, specifically, on one side of a rectangular pixel array 31, a position where the power source unit 108 and the control board 110 are provided is not limited to the form illustrated in FIG. 22. For example, the power source unit 108 and the control board 110 may be provided so as to be respectively distributed onto two facing sides of the pixel array 31 or may be provided so as to be respectively distributed onto two adjacent sides.

Figure 23:
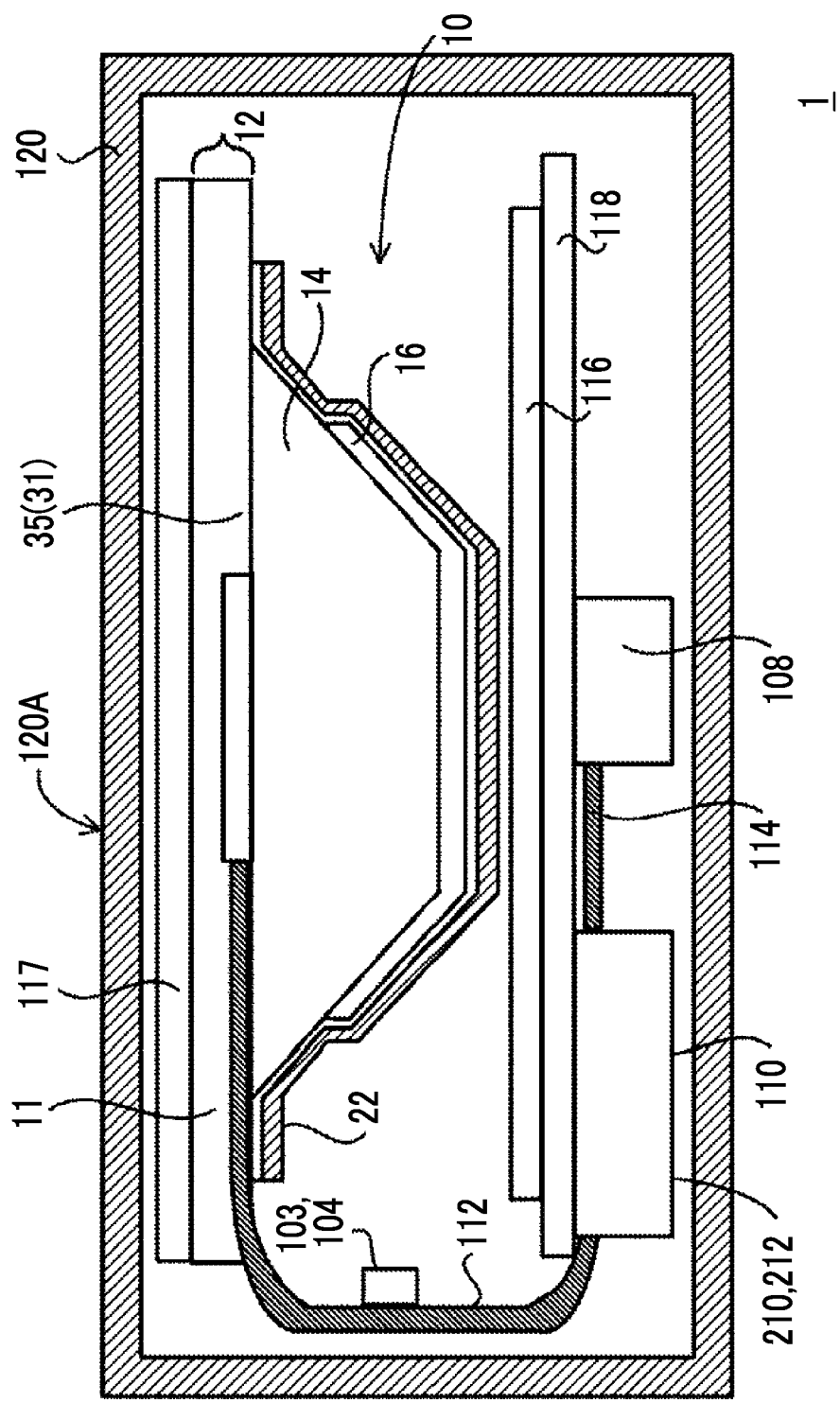
FIG. 23 is a cross-sectional view illustrating the cross-section of another example of the radiographic imaging apparatus to which the radiation detector of the exemplary embodiment is applied.

Additionally, a cross-sectional view of another example in a state where the radiation detector 10 of the first exemplary embodiment is applied to the irradiation side sampling type radiographic imaging apparatus 1 is illustrated in FIG. 23.

As illustrated in FIG. 23, the power source unit 108 and the control board 110 are provided side by side in the direction intersecting the incidence direction of radiation within the housing 120, and the radiation detector 10, the power source unit 108, and the control board 110 are provided side by side in the incidence direction of radiation.

Additionally, in the radiographic imaging apparatus 1 illustrated in FIG. 23, a base 118 that supports the radiation detector 10 and the control board 110 is provided between the control board 110 and the power source unit 108, and the sheet 116. For example, carbon or the like is used for the base 118.

In addition, it goes without saying that the configurations, manufacturing methods, and the like of the radiation detectors 10 that are described in the above respective exemplary embodiments are merely examples, and can be changed in accordance with situations without departing from the scope of the present disclosure.

The disclosure of JP2018-119355 is incorporated into the present specification by reference in its entirety.

All documents, patent applications, and technical standards described in the present specification are incorporated in the present specification by reference in their entireties to the same extent as in a case where the individual documents, patent applications, and technical standards are specifically and individually written to be incorporated by reference.

What is claimed is:

1. A radiation detector comprising a portion in which
   a substrate in which a plurality of pixels for accumulating electric charges generated in accordance with light converted from radiation are formed in a pixel region,
   a conversion layer that converts the radiation into light,
   a reflective pressure sensitive adhesive layer that reflects the light converted by the conversion layer,
   an adhesive layer that covers a region including a region ranging from an end part of the pressure sensitive adhesive layer to a surface of the substrate
   are provided in this order
   wherein the conversion layer includes a peripheral edge part and a central region, the peripheral edge part having an inclination such that a thickness of the conversion layer decreases toward an outer side, and
   wherein the adhesive layer covers the entire central region of the conversion layer and a portion of the peripheral edge part of the conversion layer, and the end part of the pressure sensitive adhesive layer is located at the peripheral edge part of the conversion layer.

2. The radiation detector according to claim 1, wherein:
   the pressure sensitive adhesive layer is formed on a base material, and
   the pressure sensitive adhesive layer is disposed on the conversion layer side.

3. The radiation detector according to claim 2, wherein the base material has reflectivity.

4. The radiation detector according to claim 1, wherein the pressure sensitive adhesive layer is a pressure sensitive adhesive resin in which an inorganic white powder is dispersed.

5. The radiation detector according to claim 1, wherein the pressure sensitive adhesive layer has a laminated structure in which a reflective and metallic first pressure sensitive adhesive film and a reflective and resinous second pressure sensitive adhesive film are laminated, and the second pressure sensitive adhesive film is disposed on the conversion layer side.

6. The radiation detector according to claim 1, further comprising a protective layer that covers the pressure sensitive adhesive layer and the conversion layer.

7. The radiation detector according to claim 6, wherein the protective layer has a laminated structure in which a polyethylene terephthalate film and an aluminum film are laminated.

8. The radiation detector according to claim 6, further comprising a reinforcing substrate provided on at least one of the protective layer side or the substrate side of a laminate including the substrate, the conversion layer, the pressure sensitive adhesive layer, and the protective layer.

9. The radiation detector according to claim 8, wherein the reinforcing substrate has higher stiffness than the substrate.

10. The radiation detector according to claim 1, wherein a central region of the conversion layer covers the pixel region of the substrate and is larger than the pixel region of the substrate.

11. The radiation detector according to claim 1, wherein a central region of the conversion layer covers the pixel region of the substrate and is smaller than the pixel region of the substrate.

12. The radiation detector according to claim 1, wherein the substrate has flexibility.

13. A radiographic imaging apparatus comprising:
    the radiation detector according to claim 1;
    a control unit that outputs a control signal for reading out electric charges accumulated in the plurality of pixels;
    a drive unit that reads out the electric charges from the plurality of pixels in accordance with the control signal; and
    a signal processing unit that receives electrical signals according to the electric charges read from the plurality of pixels and generates image data according to the received electrical signals to output the image data to the control unit.

* * * * *